(12) United States Patent
Hagiwara et al.

(10) Patent No.: US 8,581,009 B2
(45) Date of Patent: *Nov. 12, 2013

(54) 2-(ALKYLCARBONYLOXY)-1,1-DIFLUOROETHANESULFONIC ACID SALT AND METHOD FOR PRODUCING THE SAME

(75) Inventors: Yuji Hagiwara, Kawagoe (JP); Masashi Nagamori, Fujimino (JP); Masaki Fujiwara, Kawagoe (JP); Jonathan Joachim Jodry, Kawagoe (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 309 days.

This patent is subject to a terminal disclaimer.

(21) Appl. No.: 12/678,250

(22) PCT Filed: Sep. 5, 2008

(86) PCT No.: PCT/JP2008/066042
§ 371 (c)(1),
(2), (4) Date: Nov. 2, 2010

(87) PCT Pub. No.: WO2009/037981
PCT Pub. Date: Mar. 26, 2009

(65) Prior Publication Data
US 2011/0034721 A1 Feb. 10, 2011

(30) Foreign Application Priority Data

Sep. 18, 2007 (JP) ................ 2007-241606
Aug. 19, 2008 (JP) ................ 2008-210510

(51) Int. Cl.
*C07C 31/34* (2006.01)

(52) U.S. Cl.
USPC ............ 568/842; 562/108; 562/111; 560/232

(58) Field of Classification Search
None
See application file for complete search history.

(56) References Cited

U.S. PATENT DOCUMENTS

| | | | |
|---|---|---|---|
| 2,852,554 A | 9/1958 | England | |
| 6,749,987 B2 | 6/2004 | Kodama et al. | |
| 6,893,792 B2 | 5/2005 | Miya et al. | |
| 7,435,526 B2 | 10/2008 | Kodama et al. | |
| 8,110,711 B2 * | 2/2012 | Jodry et al. | ............ 568/842 |
| 2006/0228648 A1 | 10/2006 | Ohsawa et al. | |
| 2007/0003871 A1 | 1/2007 | Kodama et al. | |
| 2007/0264596 A1 | 11/2007 | Ohsawa et al. | |
| 2009/0148791 A1 | 6/2009 | Kodama et al. | |
| 2009/0234155 A1 | 9/2009 | Oh et al. | |
| 2009/0291390 A1 | 11/2009 | Jung et al. | |
| 2010/0035185 A1 | 2/2010 | Hagiwara et al. | |
| 2010/0075256 A1 | 3/2010 | Joo et al. | |
| 2010/0304303 A1 | 12/2010 | Maeda et al. | |
| 2011/0015431 A1 | 1/2011 | Jodry et al. | |

FOREIGN PATENT DOCUMENTS

| | | |
|---|---|---|
| JP | 2002-214774 A | 7/2002 |
| JP | 2004-4561 A | 1/2004 |
| JP | 2004-117959 A | 4/2004 |
| JP | 2007-145797 A | 6/2007 |
| JP | 2007-304490 A | 11/2007 |
| WO | WO 2008/099869 A1 | 8/2008 |

OTHER PUBLICATIONS

Chinese Office Action with Japanese translation dated Jul. 4, 2012 (nine (9) pages).
J.M.G. Cowie, et al., "Novel single ion, comb-branched polymer electrolytes", Solid State Ionics, 1999, pp. 233-242, vol. 123.
International Search Report dated Nov. 25, 2008 (partial translation) and PCT/ISA/237 (Twelve (12) pages).

* cited by examiner

*Primary Examiner* — Sudhakar Katakam
(74) *Attorney, Agent, or Firm* — Crowell & Moring LLP

(57) ABSTRACT

By using an organic base when a carboxylic acid bromodifluoroethyl ester is sulfinated by using a sulfinating agent, there is obtained 2-(alkylcarbonyloxy)-1,1-difluoroethanesulfinic acid ammonium salt. By oxidizing the 2-(alkylcarbonyloxy)-1,1-difluoroethanesulfinic acid ammonium salt, there is obtained 2-(alkylcarbonyloxy)-1,1-difluoroethanesulfonic acid ammonium salt. By using the 2-(alkylcarbonyloxy)-1,1-difluoroethanesulfonic acid ammonium salt as a raw material and exchanging it into an onium salt directly or through saponification/esterification, there can be obtained a 2-alkylcarbonyloxy-1,1-difluoroethanesulfonic acid onium salt.

4 Claims, No Drawings

2-(ALKYLCARBONYLOXY)-1, 1-DIFLUOROETHANESULFONIC ACID SALT AND METHOD FOR PRODUCING THE SAME

TECHNICAL FIELD

The present invention relates to a process for producing a fluorine-containing sulfonic acid salt useful as an intermediate for producing a photoacid generator useful as a chemically amplified resist material suitable for a micro-processing technology, particularly photolithography, in the production steps of semiconductor devices and the like. Moreover, the present invention relates to a process for producing a fluorine-containing sulfonic acid onium salt that functions as the photoacid generator.

BACKGROUND OF THE INVENTION

In recent years, the trend toward micro-scale pattern rule has been increasing with the trend toward large-scale integration and high-speed of LSI. The trend toward a shorter wavelength of the exposure light source lies behind it. For example, it has become possible to mass-produce DRAM (dynamic random-access memory) of 64M-bit (processing dimension is 0.25 μm or less) by the wavelength shortening from mercury lamp i-line (365 nm) to KrF excimer laser (248 nm). Furthermore, in order to realize the production of DRAM's having integration degrees of 256M and 1 G or greater, a lithography using ArF excimer laser (193 nm) has been used.

As a resist suitable for such exposure wavelength, "chemically amplified resist material" attracts much attention. This contains a radiosensitive acid generator (hereinafter referred to as "photoacid generator") which generates an acid by radiation irradiation (hereinafter, referred to as "exposure"), and is a pattern-forming material that forms a pattern by making a difference in solubility in developing agent between the exposed portion and the unexposed portion through a reaction using the acid generated by the exposure as a catalyst.

Also concerning the photoacid generator used for such a chemically amplified resist material, studies have been made variously. It has been known that, in a case where the photoacid generator as has been used for a conventional chemically amplified resist material whose light source is KrF excimer laser light to generate alkane or arenesulfonic acid is used as a component of the above-mentioned ArF-type chemically amplified resist material, the acid strength is not sufficient to cleave an acid-unstable group so as not to allow resolution entirely, or that the sensitivity is so low as to make it unsuitable for the device production.

Therefore, as the photoacid generator for the ArF-type chemically amplified resist material, those that generate perfluoroalkanesulfonic acid high in acid strength are commonly used; however, perfluorooctane sulfonic acid and derivatives thereof, which are known as PFOS abbreviated by their initials, causes problems of stability (non-degradability) stemmed from a C—F bond and of biological concentration and accumulation stemmed from hydrophobicity or lipophilicity. Additionally, perfluoroalkanesulfonic acid having 5 or more carbon atoms and derivatives thereof also begin to cause the above problems.

In order to address the above problems regarding PFOS, there has been developed, at all parts, partially fluorinated alkanesulfonic acids having a reduced degree of fluorine substitution. For instance, alkoxycarbonylfluoromethanesulfonic acid onium salts such as triphenylsulfonium methoxycarbonyldifluoromethane sulfonate (Patent Document 1), (4-methylphenyl)diphenylsulfonyl t-butoxycarbonyldifluoromethane sulfonate (Patent Document 2) and triphenylsulfonium (adamant-1-ylmethyl)oxycarbonyldifluoromethane sulfonate (Patent Document 3) have been developed as the acid generator.

On the other hand, triphenylsulfonium 1,1,3,3,3-pentafluoro-2-benzoyloxypropane-1-sulfonate, which is a kind of alkylcarbonyloxyalkanesulfonic acid onium salt and has an ester bond opposite to that of the above-mentioned alkoxycarbonyldifluoromethanesulfonic acid onium salt, and the like have been developed (Patent Document 4).

The present applicant has found a 2-alkylcarbonyloxy-1,1-difluoroethanesulfonic acid onium salt represented by the formula [5] or [10] and having three less fluorine atoms than the acid generators presented by the Patent Documents so as to be considered to less affect the environment even though identical with the alkylcarbonyloxyalkanesulfonic acid onium salt. Additionally, the present applicant found this substance to function as an acid generator having a high acid strength with the minimum possible number of fluorine atom, and to be excellent in compatibility with solvents or resins so as to be useful as the acid generator for the resist material, and therefore already filed patent applications (Japanese Patent Application No. 2007-143879 and Japanese Patent Application No. 2007-143880).

By the way, as a method for synthesizing the above-mentioned alkoxycarbonyldifluoromethanesulfonic acid onium salt, a reaction path as represented by the following conventional equation [1]

[Chemical Formula 1]

EQUATION [1]

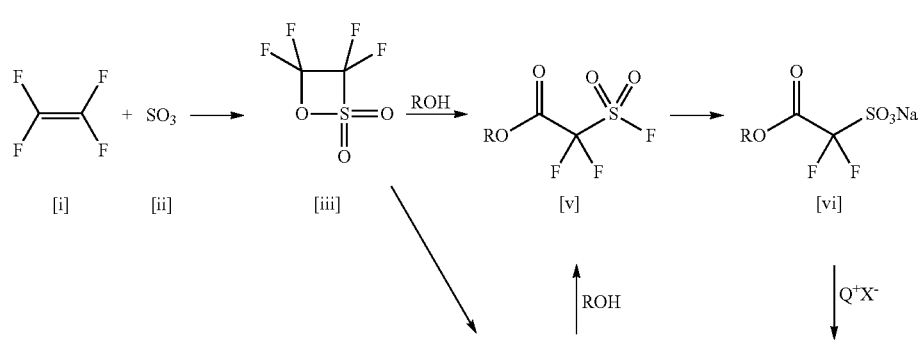

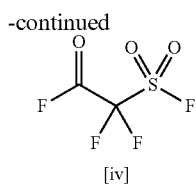

[iv]

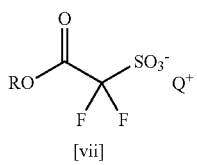

[vii]

has been known. More specifically, the path starts from synthesizing 3,3,4,4-tetrafluoro-[1,2]oxathietane 2,2-dioxide [iii] in the first place from tetrafluoroethylene [i] and sulfur trioxide [ii], and includes: synthesizing [v] by a ring-opening reaction of [iii] with the use of alcohol (ROH) or passing an acid fluoride [iv] through ring-opening isomerization of [iii] and then passing esterification of [iv] with the use of alcohol (ROH); subsequently converting [v] into a sulfonic acid (a sulfonic acid sodium salt) [vi] with the use of a basic metal salt (mainly sodium hydroxide); and thereafter conducting an onium-salt exchange with the use of an onium salt ($Q^+X^-$: Q is a monovalent onium cation and X is mainly halogen) such as a sulfonium salt thereby obtaining the target acid generator alkoxycarbonyldifluoroalkanesulfonic acid onium salt [vii] (Patent Document 1 and Patent Document 5).

On the other hand, as a method for synthesizing a 1,1,3,3,3-pentafluoro-2-benzoyloxypropane-1-sulfonic acid onium salt discussed in Patent Document 4, a reaction path as represented by the following equation [2] is disclosed.

[Chemical Formula 2]

EQUATION [2]

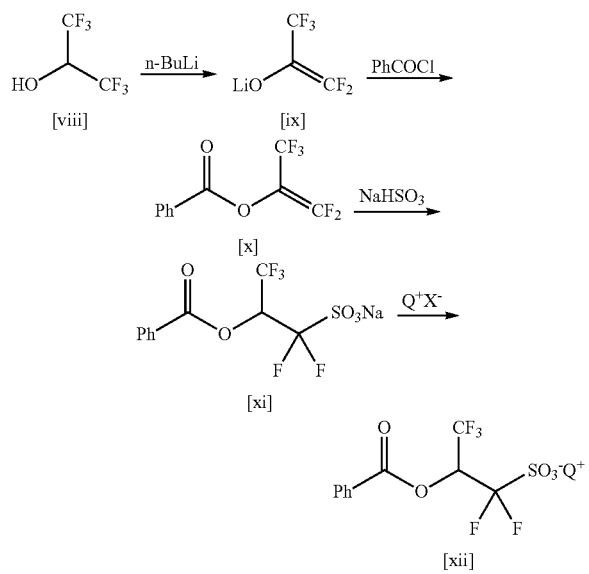

However, hitherto known methods for producing a 2-alkylcarbonyloxy-1,1-difluoroethanesulfonic acid salt have been very few, which means that hitherto known methods for producing 2-(alkylcarbonyloxy)-1,1-difluoroethanesulfonic acid onium salt have been very few.

Patent Document 1: Japanese Patent Application Publication No. 2004-117959
Patent Document 2: Japanese Patent Application Publication No. 2002-214774
Patent Document 3: Japanese Patent Application Publication No. 2004-4561
Patent Document 4: Japanese Patent Application Publication No. 2007-145797
Patent Document 5: U.S. Pat. No. 2,852,554
Non-Patent Document 1: Solid State Ionics, 1999, Volume 123, pages 233-242

SUMMARY OF THE INVENTION

The above-mentioned method for producing the alkoxycarbonyldifluoromethanesulfonic acid salt uses 3,3,4,4-tetrafluoro-[1,2] oxathietane 2,2-dioxide [iii] synthesized from tetrafluoroethylene [i] and sulfur trioxide [ii] as the raw material. As conventionally known, tetrafluoroethylene [i] is high in chemical reactivity and has the danger of explosion so as to be hard to handle in large quantity. Additionally, sulfur trioxide [ii] is an oxidizing agent so strong as to violently react with flammable substances, reducing substances and organic compounds, and therefore brings the load of handling in large quantity. This synthesizing method in which reagents having difficulty in handling in large quantity are mixed needs an enough attention to safety. This is therefore a reaction high in degree of industrial difficulty, so that the obtained 3,3,4,4-tetrafluoro-[1,2]oxathietane 2,2-dioxide [iii] becomes very expensive, necessarily.

In addition, there is a problem where hydrogen fluoride or fluoride salt is produced in large quantity as a by-product of the conversion reaction of the acid fluoride ([iv] or [v]). A fluorine ion liberated from hydrogen fluoride or fluoride salt corrodes and devitrifies a glass reactor. Additionally, not only hydrogen fluoride itself but also hydrogen fluoride (a strong acid) generated by contact between fluoride salt and an acid makes metallic reactors such as iron and stainless steel unusable, so that usable materials for reactors are greatly limited.

Thus, there exist some disadvantages in producing the alkoxycarbonyldifluoromethanesulfonic acid salt.

On the other hand, in Patent Document 4, 1,1,1,3,3,3-hexafluoro-2-propanol [viii] having 6 fluorine atoms serves as the starting material to construct a 1,1,3,3,3-pentafluoro-2-benzoyloxypropane-1-sulfonic acid salt [xi] as represented by the above equation [3]. Upon this, the sulfonic acid salt is led to be a 1,1,3,3,3-pentafluoro-2-benzoyloxypropane-1-sulfonic acid onium salt [xii]. This synthesizing method is characterized by passing an enolate represented by [ix] as an intermediate active species. An enolate ion is, generally, a chemical species which is hard to exist stably. However, in the compound of Patent Document 5 whose $CF_3$ group bonding to carbon of C=C double bond has a strong electron-attracting property, the enolate is stabilized, with which the above reaction is allowed as a result.

Meanwhile, the substrate of the present invention whose moiety corresponding to this "$CF_3$ group" is "H" is therefore largely reduced in electron withdrawal against a double bond moiety. As a result, an enolate ion corresponding thereto becomes unstable so as to make it difficult to perform a reaction corresponding to the reaction of the Patent Document (see the following equation).

[Chemical Formula 3]

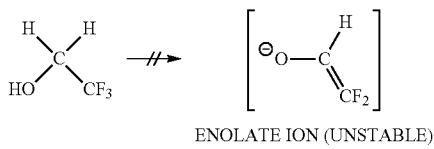

ENOLATE ION (UNSTABLE)

In actual fact, there has never been known a method for obtaining 2,2-difluoroethen-1-yl aliphatic carboxylic acid ester or aromatic carboxylic acid ester by using 2,2,2-trifluoroethanol as the starting material. Furthermore, there has never been found a report that an enolate salt [CF$_2$=CHOM (M=Li, K, Na)] serving as a precursor of these is formed.

Concerning the production of alkylcarbonyloxyalkanesulfonic acid, a production method of compound having a great number of fluorine atoms such as 1,1,3,3,3-pentafluoro-2-benzoyloxypropane-1-sulfonic acid salt has been known; however, a production method of 2-alkylcarbonyloxy-1,1-difluoroethanesulfonic acid salt having 2 fluorine atoms has never been known.

The above-mentioned is so summarized: that a difluoroalkanesulfonic acid skeleton having 2 fluorine atoms preferably serves as an alkanesulfonic acid salt having a sufficient acid strength with a lower number of fluorine atom: that the conventional process of producing alkoxycarbonyldifluoromethanesulfonic acid salt however has disadvantages; and that the process of producing 2-alkylcarbonyloxy-1,1-difluoroethanesulfonic acid salt in particular has never been known.

Consequently, the establishment of the industrial production method capable of economically and readily producing the difluoroalkanesulfonic acid skeleton having 2 fluorine atoms has been desired.

In view of the above, an object of the present invention is to provide a method for economically and readily producing 2-alkylcarbonyloxy-1,1-difluoroethanesulfonic acid salt useful as the photoacid generator used for the chemically amplified resist material.

The present inventors have eagerly made studies in order to achieve the above object. As a result, they have found novel compounds useful for producing the above-mentioned "2-(alkylcarbonyloxy)-1,1-difluoroethanesulfonic acid onium salt". Furthermore, they have found a novel reaction route extremely useful for a large-scale synthesis as compared with the conventional methods which route passes through these novel compounds.

The present invention includes [Embodiment 1] to [Embodiment 4] as will be discussed below.

[Embodiment 1]

To begin with, studies were made on a method for synthesizing 2-alkylcarbonyloxy-1,1-difluoroethanesulfonic acid ammonium salt, a raw material compound common in all of the present invention.

In order to obtain an end difluoroalkylsulfinic acid salt by sulfinating an end bromodifluoroalkyl group, there has hitherto been adopted a method generally using sodium dithionite as a sulfinating agent in a mixture solvent of water and a polar solvent such as N,N-dimethylformamide (DMF), acetonitrile and methanol. In this case, a sulfinated substance is obtained as a sulfonic acid sodium salt. (For example, Journal of Fluorine Chemistry, Volume 67, pages 233-234, 1994.)

Also in a case of a carboxylic acid bromodifluoroethyl ester represented by the following formula [1], a corresponding sulfinic acid sodium salt represented by the following formula [13] can be obtained by using sodium dithionite in mixture solvent of water and a polar solvent such as N,N-dimethylformamide (DMF), acetonitrile and methanol.

[Chemical Formula 4]

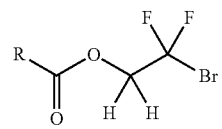

[1]

(In the above formula [1], R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. However, those who have in its R structure an unconjugated unsaturated moiety (a double or triple bond) are excepted.)

[Chemical Formula 5]

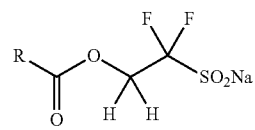

[13]

(In the Above Formula [13], R is Synonymous with R of the Formula [1].)

However, this reaction does not develop at all according to a combination of solvents, as is the result discussed in Journal of Fluorine Chemistry, Volume 67, pages 233-234, 1994. When a reaction solution is homogeneous as is the combination of water and ethanol, it is difficult to completely terminate the reaction. In a case where the reaction solution can be separated into two layers (an organic layer and a water layer) by suitably arranging conditions, the reaction can be terminated only by separating the water layer from the reaction solution in the reaction and by adding water and sodium dithionite again (see Comparative Example 1-1 and Comparative Example 1-2).

Moreover, it is required to distill a solvent containing a large amount of water off in order to extract the target sulfinic acid sodium salt after the reaction, which becomes a significant burden. Additionally, if condensation of the reaction solution is developed without removing fluorine ion generated by a side reaction in a trace quantity, the concentration of residual fluoride ion is gradually increased. With this, equipments are to be subjected to corrosion if these are glass. In this reaction, furthermore, bromine having gotten out of the raw material carboxylic acid bromodifluoroethyl ester exists in a system upon being converted into sodium bromide probably by sodium of sodium dithionite, which has brought about many problems; for example, if condensation is developed without removing this bromine so that the bromine is brought into the next process (i.e., the oxidation process) without being separated from the target sulfinic acid sodium salt, a by-product is sometimes generated (see Comparative Example 1-2 and Comparative Example 2-2).

In view of the above, the present inventors have eagerly made studies thereon. As a result of this, they have found to be allowed to obtain generally only an ammonium salt and not a sodium salt by adding amine together with the sulfinating agent at the time of sulfination reaction in an amount not smaller than the equivalent amount of the carboxylic acid bromodifluoroethyl ester. The ammonium salt is a novel compound represented by the following formula [2].

[Chemical Formula 6]

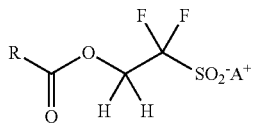

[2]

(In the formula [2], R is synonymous with R of the formula [1]. $A^+$ represents an ammonium ion derived from the above-mentioned amine.)

This sulfinic acid ammonium salt is high in lipophilicity or low in hydrophilicity so as to be readily extractable with an organic solvent. Accordingly, the present inventors have found that the problematic fluoride ion and inorganic salt such as sodium bromide can be removed by rinsing with water. They further found to be released from limitation on the reactor and to be allowed to suppress the side reaction in the next process (the oxidation process).

Furthermore, the present inventors have achieved an amazing fact that the sulfination reaction is excellently accelerated with the coexistence of the amine to be finished in a short time.

Moreover, the present inventors have achieved a finding not only that a 2-alkylcarbonyloxy-1,1-difluoroethanesulfinic acid salt can be efficiently purified by rinsing the organic layer with a thiosulfuric acid metal salt aqueous solution or a sulfurous acid metal salt aqueous solution after the above-mentioned "extraction with organic solvent" but also that generation of the by-product (i.e., the carboxylic acid bromodifluoroethyl ester represented by the formula [1] and serving as the substrate of the sulfination reaction: which ester disappears in the sulfination reaction but generated again in the oxidation process) to be formed in the expected "oxidation process" can be greatly suppressed.

The present inventors thus have found a 2-alkylcarbonyloxy-1,1-difluoroethanesulfinic acid salt useful as an intermediate for producing a photoacid generator for resist or useful as an intermediate for producing a solid polymeric electrolyte for fuel cell, a novel production method thereof suitable for a large-scale production, and a purification method thereof.

[Embodiment 2]

First of all, it has been found that a 2-(alkylcarbonyloxy)-1,1-difluoroethanesulfonic acid ammonium salt represented by the formula [3] can be obtained by providing a 2-alkylcarbonyloxy-1,1-difluoroethanesulfinic acid ammonium salt represented by the formula [2] and obtained by the method discussed in the above "Embodiment 1" (also referred to as "1st process") to the oxidation process as the 2nd process.

[Chemical Formula 7]

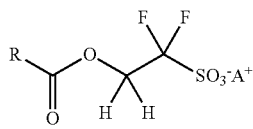

[3]

(In the Formula [3], R and $A^+$ are Synonymous with R and $A^+$ of the Formula [2].)

This sulfonic acid ammonium salt is novel compound so as to be high in lipophilicity or low in hydrophilicity as well as the above-mentioned sulfinic acid ammonium salt, as expected; therefore, this salt can be readily extracted with an organic solvent. The present inventors, accordingly, have achieved a finding that a high purity sulfonic acid ammonium salt can be obtained by rinsing a water-soluble and inorganic salt-containing impurity to remove it.

Thus, the present inventors have found a 2-alkylcarbonyloxy-1,1-difluoroethanesulfonic acid salt useful as an intermediate for producing a photoacid generator for resist or useful as an intermediate for producing a solid polymeric electrolyte for fuel cell, a novel production method thereof suitable for a large-scale production, and a purification method thereof.

[Embodiment 3]

It has been found that a 2-alkylcarbonyloxy-1,1-difluoroethanesulfonic acid onium salt represented by the formula [5] can be obtained by providing the 2-alkylcarbonyloxy-1,1-difluoroethanesulfonic acid ammonium salt represented by the formula [3] and synthesized by the method discussed in the above "Embodiment 2" to "an onium-salt exchanging process 1 (a 3rd process)" (see the following equation [3]).

[Chemical Formula 8]

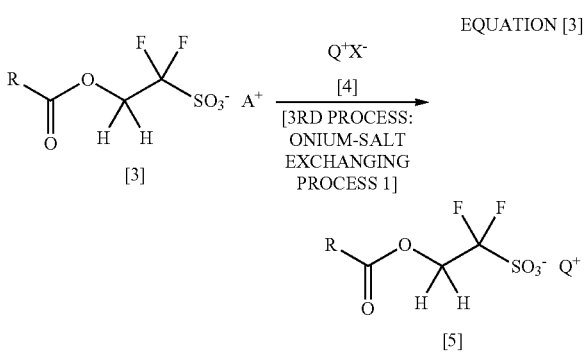

EQUATION [3]

(In the above equation [3], R and $A^+$ are synonymous with R and $A^+$ of the formula [2]. $X^-$ is a monovalent anion. $Q^+$ is a sulfonium cation represented by the following formula (a) or the following formula (b), or an iodonium cation represented by the following formula (c))

[Chemical Formula 9]

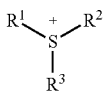
(a)

In the formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Furthermore, any two or more of $R^2$ and $R^3$ may bond to each other to form a ring together with a sulfur atom shown in this formula.

[Chemical Formula 10]

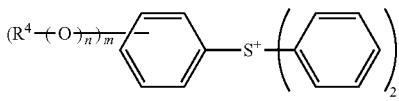
(b)

In the formula (b), $R^4$ represents a substituted or unsubstituted linear, branched or cyclic alkyl group or alkenyl group having 1 to 20 carbon atoms or a substituted or unsubstituted aryl group having 6 to 14 carbon atoms. m represents an integer of from 1 to 5, and n represents 0 (zero) or 1.

[Chemical Formula 11]

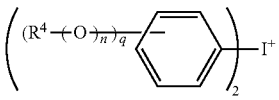
(c)

In the formula (c), $R^4$ represents a substituted or unsubstituted linear, branched or cyclic alkyl group or alkenyl group having 1 to 20 carbon atoms or a substituted or unsubstituted aryl group having 6 to 14 carbon atoms. q represents an integer of from 0 (zero) to 5, and n represents 0 (zero) or 1.

Namely, with the method discussed in "Embodiment 3", it becomes possible to synthesize the 2-alkylcarbonyloxy-1,1-difluoroethanesulfonic acid onium salt useful as the photoacid generator used for the chemically amplified resist material.

[Embodiment 4]

As has been discussed, there is a limitation on the kind of the functional group R of a compound synthesized by the method discussed in "Embodiment 3". In other words, the kind of the functional group R is "a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. However, those who have in its R structure an unconjugated unsaturated moiety (a double or triple bond) are excepted.)", so that compounds having in its structure the unconjugated unsaturated moiety (the double or triple bond) as R, other than aromatic rings having a conjugated unsaturated moiety such as aryl group and heteroaryl group, are excepted, which results from the 3rd process (a sulfination process). The present inventors have found that, if the compounds having in its structure the unconjugated unsaturated moiety (the double or triple bond) as R are used as the raw material for the 3rd process (the sulfination process), the unconjugated unsaturated moiety causes a side reaction so as to make it difficult to obtain the target sulfinated substance.

Examples of R having the unconjugated unsaturated moiety (the double or triple bond) are linear, branched or cyclic alkenyl groups. Concrete examples of the alkenyl groups include vinyl group, allyl group, 1-methylethenyl group, 1-methylallyl group, 2-methylallyl group, 1-propenyl group, isopropenyl group, 2-butenyl group, 3-butenyl group, 1,3-butadienyl group, 2-pentenyl group, 4-pentenyl group, 2-hexenyl group, 5-hexenyl group, cyclopropenyl group, cyclopentenyl group, cyclohexenyl group and 5-norbornen-1-yl group (the following equation [4] and the equation [5]; Comparative Example [3] and Comparative Example [4]).

[Chemical Formula 12]

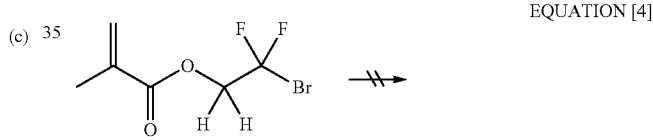
EQUATION [4]

EQUATION [5]

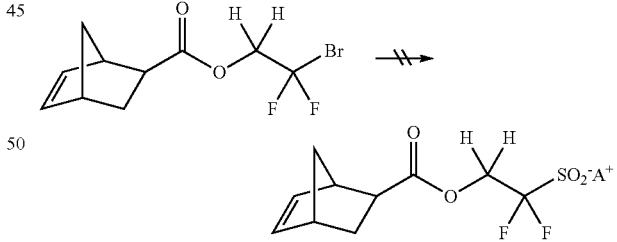

In view of the above circumstances, the present inventors found the novel synthesis route in which a 2-alkylcarbonyloxy-1,1-difluoroethanesulfonic acid salt represented by the formula [2] and obtained in the above-mentioned [Embodiment 2] is used as the starting material, and reached the finding that the above problems can be solved by taking this route.

More specifically, it has been found that a 2-alkylcarbonyloxy-1,1-difluoroethanesulfonic acid onium salt useful as a photoacid generator for a resist material and represented by the formula [10]

[Chemical Formula 18]

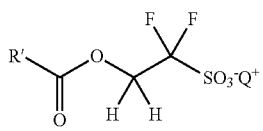

[10]

is obtained: by providing the 2-alkylcarbonyloxy-1,1-difluoroethanesulfonic acid ammonium salt represented by the formula [3] and obtained by the above-mentioned [Embodiment 2] to a saponification reaction (or hydrolysis reaction in the presence of a basic substance), thereby obtaining a 2-hydroxy-1,1-difluoroethanesulfonic acid salt represented by the formula [6]

[Chemical Formula 13]

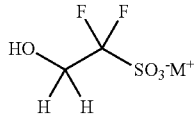

[6]

(in the above formula [6], $M^+$ represents a counter cation) (a 3'th process: a saponification process); subsequently by reacting the 2-hydroxy-1,1-difluoroethanesulfonic acid salt with a carboxylic acid derivative represented by the formula [7]

[Chemical Formula 14]

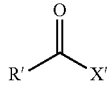

[7]

(In the above formula [7], X' represents a hydroxyl group or a halogen. R represents a linear or branched alkyl group having 1 to 10 carbon atoms having a polymerizable double bond at least at the end moiety, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. Furthermore, one of hydrogen atoms on the alkyl group may be substituted with a 2-acryloyloxy group or a 2-methacryloyloxy group.) or the formula [8]

[Chemical Formula 15]

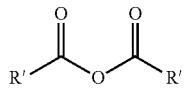

[8]

(In the above formula [8], R' is synonymous with R' of the formula [7].) (a 4th process: an esterification process 2) thereby obtaining a 2-(alkylcarbonyloxy)-1,1-difluoroethanesulfonic acid salt represented by the formula [16]

[Chemical Formula 16]

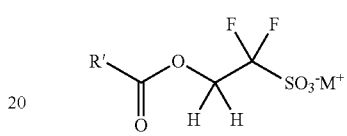

[9]

(In the above formula [9], $M^+$ is synonymous with $M^+$ of the formula [6]. R' is synonymous with R' of the formula [7].); and by carrying out an onium-salt exchange thereon by using a monovalent onium salt represented by the formula [4]

[Chemical Formula 17]

$Q^+X^-$ [4]

(a 5th process: an onium-salt exchanging process 2).

[Chemical Formula 19]

EQUATION [6]

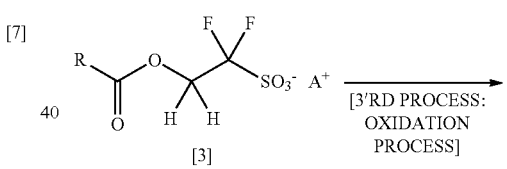

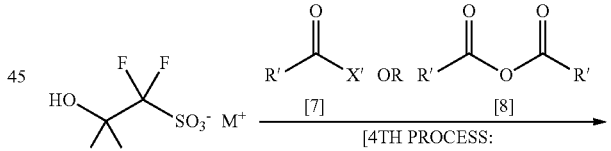

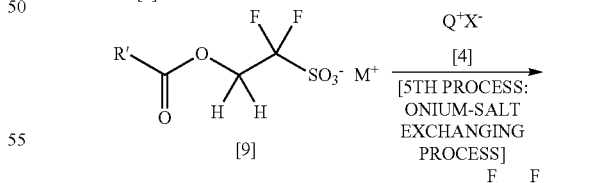

In the reaction, an important point is that a substituent R' of the 2-alkylcarbonyloxy-1,1-difluoroethanesulfonic acid onium salt represented by the formula [10] includes "those who have in its structure the unconjugated unsaturated moiety (the double or triple bond)". Namely, among the 2-alkylcarbonyloxy-1,1-difluoroethanesulfonic acid onium salt useful as the photoacid generator used for chemically amplified resist material, this "Embodiment 4" is useful especially for those who have in its structure the unconjugated unsaturated moiety (the double or triple bond) as the substituent R'.

Particularly, those having the unconjugated unsaturated moiety at the end of the substituent, i.e. a 2-(ω-alkenylcarbonyloxy)-1,1-difluoroethenesulfonic acid onium salt, can be fixed in a resist resin by being copolymerized with other monomer and therefore can be used as "a photoacid generator of a type carried by the resist resin", as well as a polymerizable and fluorine-containing sulfonic acid onium salt disclosed in International Patent Application Publication No. 2006/121096 A1. Such a "photoacid generator of the type carried by the resist resin" is a new type of photoacid generator who has recently been receiving attention because of its high performances such as a high resolution. Also in such a sense, the 2-(ω-alkenylcarbonyloxy)-1,1-difluoroethenesulfonic acid onium salt having the unconjugated unsaturated moiety at the end of its substituent is extremely useful.

As discussed above, a suitable selection of [Embodiment 1] to [Embodiment 4] makes it possible to produce 2-alkylcarbonyloxy-1,1-difluoroethane sulfonic acid salts useful as the intermediate for the acid generator used for the resist material or as the intermediate for the electrolyte for the fuel cell and additionally to produce 2-alkylcarbonyloxy-1,1-difluoroethanesulfonic acid onium salts useful as the photoacid generator, with regard to compounds of wide kinds of substituents. The present invention has thus achieved its completion.

The present invention, in which all necessary raw materials are inexpensive and the operation in any of the processes is so convenience as to be able to perform with a less operational burden, is much more advantageous than the conventional means from the viewpoint of the industrial-scale production of the target 2-alkylcarbonyloxy-1,1-difluoroethanesulfonic acid salts.

According to the present invention, there is provided a sulfinic acid ammonium salt represented by the following formula [2].

[Chemical Formula 20]

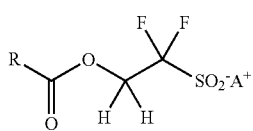

[2]

(In the above formula [2], A$^+$ represents an ammonium ion while R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. However, those who have in its R structure an unconjugated unsaturated moiety (a double or triple bond) are excepted.)

According to the present invention, furthermore, there is provided a sulfonic acid ammonium salt represented by the following formula [3].

[Chemical Formula 21]

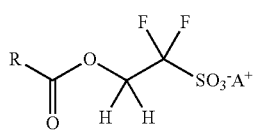

[3]

(In the above formula [3], A$^+$ represents an ammonium ion while R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. However, those who have in its R structure an unconjugated unsaturated moiety (a double or triple bond) are excepted.)

In the above formula [2] or [3], A$^+$ may be an ammonium ion represented by the formula [I].

[Chemical Formula 22]

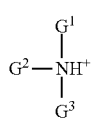

[I]

(In the above formula [I], G$^1$, G$^2$ and G$^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms. Additionally, at least two or more of G$^1$, G$^2$ and G$^3$ may represent a ring which may include a hetero atom.)

According to the present invention, there are provided triethylammonium 2-(1-adamantane)carbonyloxy-1,1-difluoroethanesulfonate and triethylammonium 1,1-difluoro-2-(pivaloyloxy)ethanesulfonate, both of which correspond to the sulfonic acid ammonium salt represented by the formula [3].

According to the present invention, there is provided a method (a first method) for producing a 2-(alkylcarbonyloxy)-1,1-difluoroethanesulfinic acid ammonium salt represented by the formula [2]

[Chemical Formula 24]

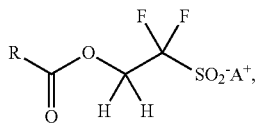

[2]

comprising the step of reacting a carboxylic acid bromodifluoroethyl ester represented by the following formula [1]

[Chemical Formula 23]

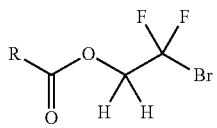

[1]

with a sulfinating agent in the presence of an amine.
(In the above formula [1] and the formula [2], R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. However, those who have in its R structure an unconjugated unsaturated moiety (a double or triple bond) are excepted.) $A^+$ represents an ammonium ion.

There is provided a method (a second method) for producing a 2-(alkylcarbonyloxy)-1,1-difluoroethanesulfonic acid ammonium salt represented by the formula [3]

[Chemical Formula 25]

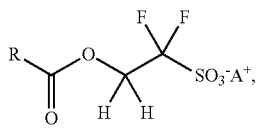

[3]

comprising the following two processes.
A 1st process (a sulfination process): a process of reacting a carboxylic acid bromodifluoroethyl ester represented by the following formula [1]

[Chemical Formula 26]

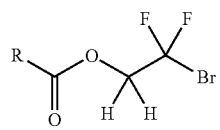

[1]

with a sulfinating agent in the presence of an amine thereby obtaining a 2-(alkylcarbonyloxy)-1,1-difluoroethanesulfinic acid ammonium salt represented by the formula [2]

[Chemical Formula 27]

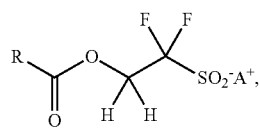

[2]

A 2nd process (an oxidation process): a process of reacting the 2-(alkylcarbonyloxy)-1,1-difluoroethanesulfinic acid ammonium salt represented by the formula [2] and obtained by the 1st process (the sulfination process) with an oxidizing agent thereby obtaining a 2-(alkylcarbonyloxy)-1,1-difluoroethanesulfonic acid ammonium salt represented by the formula [3].
(In the above formula [1] to the formula [3], R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group containing the alicyclic organic group and the linear alkylene group may be substituted with one oxygen atom to form a keto group. However, those who have in its R structure an unconjugated unsaturated moiety (a double or triple bond) are excepted.) $A^+$ represents an ammonium ion.)

According to the present invention, there is further provided a method (a third method) for producing a 2-(alkylcarbonyloxy)-1,1-difluoroethanesulfonic acid onium salt represented by the formula [5]

[Chemical Formula 29]

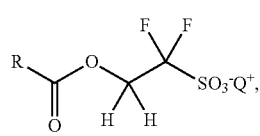

[5]

comprising the step of:

carrying out an onium-salt exchange (a 3rd process: an onium-salt exchanging process 1) on the 2-(alkylcarbonyloxy)-1,1-difluoroethanesulfonic acid ammonium salt represented by the formula [3] and obtained by the second method, by using a monovalent onium salt represented by the formula [4]

[Chemical Formula 28]

Q⁺X⁻ [4]

(In the above formula [4], X⁻ represents a monovalent anion. In the above formula [5], R is synonymous with R of the formula [1] to the formula [3]. In the above formula [4] and the formula [5], Q⁺ is a sulfonium cation represented by the following formula (a) or the following formula (b), or an iodonium cation represented by the following formula (c).

[Chemical Formula 30]

(a)

In the above formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Furthermore, any two or more of $R^1$, $R^2$ and $R^3$ may bond to each other to form a ring together with a sulfur atom shown in the formula.

[Chemical Formula 31]

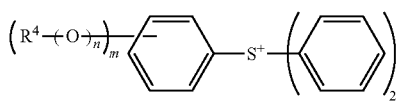

(b)

In the above formula (b), $R^4$ represents a substituted or unsubstituted linear, branched or cyclic alkyl group or alkenyl group having 1 to 20 carbon atoms or a substituted or unsubstituted aryl group having 6 to 14 carbon atoms. m represents an integer of from 1 to 5, and n represents 0 (zero) or 1.

[Chemical Formula 32]

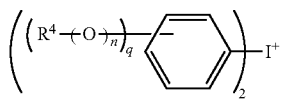

(c)

In the above formula (c), $R^4$ represents a substituted or unsubstituted linear, branched or cyclic alkyl group or alkenyl group having 1 to 20 carbon atoms or a substituted or unsubstituted aryl group having 6 to 14 carbon atoms. q represents an integer of from 0 (zero) to 5, and n represents 0 (zero) or 1.

According to the present invention, there is further provided a method (a fourth method) for producing a 2-(alkylcarbonyloxy)-1,1-difluoroethanesulfonic acid onium salt represented by the formula [10]

[Chemical Formula 38]

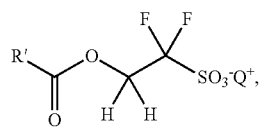

[10]

comprising the steps of:

saponifying the 2-(alkylcarbonyloxy)-1,1-difluoroethanesulfonic acid salt represented by the formula [3] and obtained by the second method, thereby obtaining a 2-hydroxy-1,1-difluoroethanesulfonic acid salt represented by the formula [6]

[Chemical Formula 33]

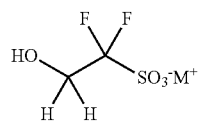

[6]

(a 3'th process: a saponification process);

subsequently reacting the 2-hydroxy-1,1-difluoroethanesulfonic acid salt with a carboxylic acid derivative represented by the formula [7]

[Chemical Formula 34]

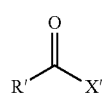

[7]

or the formula [8]

[Chemical Formula 35]

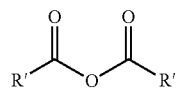

[8]

(a 4th process: an esterification process 2) thereby obtaining a 2-(alkylcarbonyloxy)-1,1-difluoroethanesulfonic acid salt represented by the formula [9]

[Chemical Formula 36]

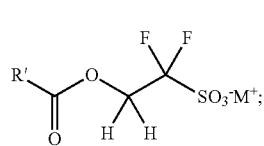

[9]

and carrying out an onium-salt exchange on the 2-(alkylcarbonyloxy)-1,1-difluoroethanesulfonic acid salt by using a monovalent onium salt represented by the formula [4]

[Chemical Formula 37]

$$Q^+X^- \quad [4]$$

(a 5th process: an onium-salt exchanging process 2).

(In the above formula [6] and the formula [9], $M^+$ represents a counter cation. In the above formula [7], X' represents a hydroxyl group or a halogen. In the above formula [7] to the formula [10], R' represents a linear or branched alkyl group having 1 to 10 carbon atoms, a linear or branched alkenyl group of 1 to 10 carbon atoms having a polymerizable double bond at least at an end moiety, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group having the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alkenyl group, the alicyclic organic group, or the organic group having the alicyclic organic group and the linear alkylene group may be substituted with one oxygen atom to form a keto group. Moreover, one of hydrogen atoms on the alkyl group may be substituted with a 2-acryloyloxy group or a 2-methacryloyloxy group.) In the above formula [10], $Q^+$ is synonymous with $Q^+$ of the formula [4] and the formula [5].)

The carboxylic acid bromodifluoroethyl ester of the first or second method may be one obtained by esterification of 2-bromo-2,2-difluoroethanol.

A rough substance of the 2-(alkylcarbonyloxy)-1,1-difluoroethanesulfinic acid ammonium salt obtained by sulfination reaction of the first or second method may be extracted with an organic solvent, and a layer comprising the organic solvent may be purified by being rinsed with water.

Additionally, a rough substance of the 2-(alkylcarbonyloxy)-1,1-difluoroethanesulfinic acid ammonium salt obtained by sulfination reaction of the first or second method may be extracted with an organic solvent, and a layer comprising the organic solvent may be purified by being rinsed with a thiosulfuric acid metal salt aqueous solution or a sulfurous acid metal salt aqueous solution.

A rough substance of the 2-(alkylcarbonyloxy)-1,1-difluoroethanesulfonic acid ammonium salt obtained by oxidation reaction of the second method may be extracted with an organic solvent, and a layer comprising the organic solvent may be purified by being rinsed with water.

DETAILED DESCRIPTION

According to the present invention, by using a carboxylic acid bromodifluoroethyl ester, there is provided the effect of conveniently producing fluorine-containing sulfonic acid salts at a high yield and on an industrial scale, the fluorine-containing sulfonic acid salts being useful as an intermediate for producing a solid electrolyte used for a fuel cell or the like or an intermediate for producing a photoacid generator useful as a chemically amplified resist material suitable for micromachining techniques (e.g. photolithography, in particular) applied in industrial processes for semiconductor devices or the like. According to the present invention, there is further provided the effect of conveniently producing fluorine-containing sulfonic acid onium salts that function as the photoacid generator, at a high yield and on an industrial scale.

Hereinafter, the present invention will be discussed in more detail.

[Sulfinic Acid Ammonium Salt]

A sulfinic acid ammonium salt of the present invention is represented by the following formula [2].

[Chemical Formula 39]

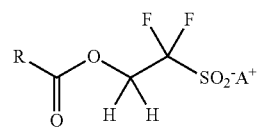

[2]

In the above formula [2], $A^+$ represents an ammonium ion. R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group having the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group having the alicyclic organic group and the linear alkylene group may be substituted with one oxygen atom to form a keto group. However, those who have in its R structure an unconjugated unsaturated moiety (a double or triple bond) are excepted.)

Concrete examples of the ammonium ion represented by $A^+$ are ammonium ion ($NH_4^+$), methylammonium ion ($MeNH_3^+$), dimethylammonium ion ($Me_2NH_2^+$), trimethylammonium ion ($Me_3NH^+$), ethylammonium ion ($EtNH_3^+$), diethylammonium ion ($Et_2NH_2^+$), triethylammonium ion ($Et_3NH^+$.), n-propylammonium ion (n-$prNH_3^+$), di-n-propylammonium ion (n-$pr_2NH_2^+$), tri-n-propylammonium ion (n-$pr_3NH^+$), i-propylammonium ion (i-$prNH_3^+$), di-i-propylammonium ion (i-$pr_2NH_2^+$), tri-ipropylammonium ion (i-$pr_3NH^+$), n-butylammonium ion (n-$BuNH_3^+$), di-n-butylammonium ion (n-$Bu_2NH_2^+$), tri-n-butylammonium ion (n-$Bu_3NH^+$), sec-butylammonium ion (sec-$BuNH_3^+$), di-sec-butylammonium ion (sec-$Bu_2NH_2^+$), tri-sec-butylammonium ion (sec-$Bu_3NH^+$), tert-butylammonium ion (t-$BuNH_3^+$), di-tert-butylammonium ion (t-$Bu_2NH_2^+$), tri-tert-butylammonium ion (t-$Bu_3NH^+$), diisopropylethylammonium (i-$Pr_2EtNH^+$), phenylammonium ion ($PhNH_3^+$), diphenylammonium ion ($Ph_2NH_2^+$), triphenylammonium ion ($Ph_3NH^+$), tetramethylammonium ion ($Me_4N^+$), tetraethylammonium ion ($Et_4N^+$), trimethylethylammonium ion ($Me_3ETN^+$), tetra-n-propylammonium ion (n-$Pr_4N^+$), tetra-i-propylammonium ion (i-$Pr_4N^+$), tetra-n-butylammonium ion (n-$Bu_4N^+$), and ions having the following structures.

[Chemical Formula 40]

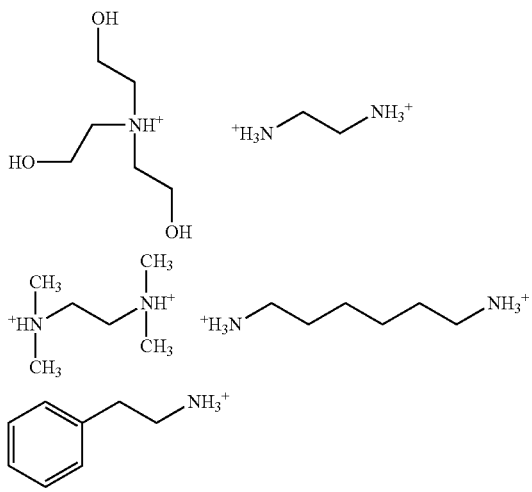

[Chemical Formula 41]

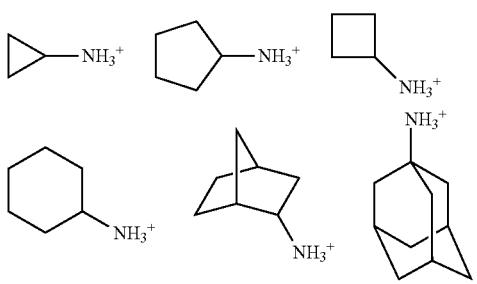

[Chemical Formula 42]

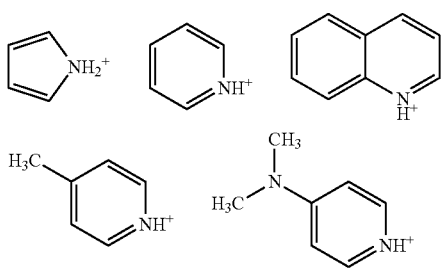

[Chemical Formula 43]

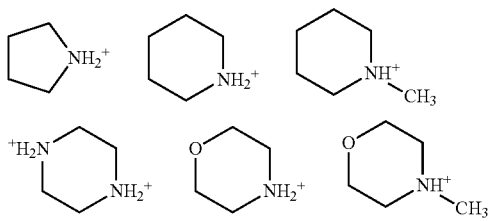

[Chemical Formula 44]

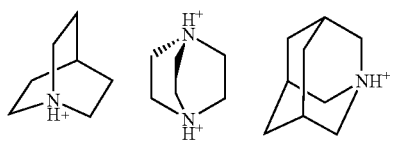

Among these, the preferable A⁺ is an ammonium ion represented by the following formula [I].

[Chemical Formula 45]

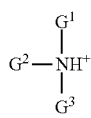

[I]

In the above formula [I], $G^1$, $G^2$ and $G^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms. Additionally, at least two or more of $G^1$, $G^2$ and $G^3$ may represent a ring which may include a hetero atom.

Concrete examples are methylammonium ion ($MeNH_3^+$), triethylammonium ion ($Et_3NH^+$, tri-n-propylammonium ion (n-$pr_3NH^+$), tri-i-propylammonium ion (i-$pr_3NH^+$), tri-n-butylammonium ion (n-$Bu_3NH^+$), tri-sec-butylammonium ion (sec-$Bu_3NH^+$), tri-tert-butylammonium ion (t-$Bu_3NH^+$), diisopropylethylammonium (n-$Pr_2EtNH^+$), triphenylammonium ion ($Ph_3NH^+$), and ions having the following structures.

[Chemical Formula 46]

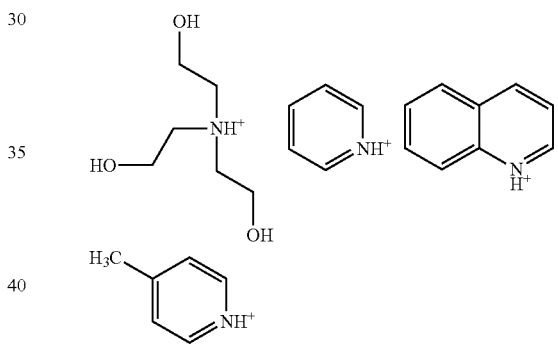

[Chemical Formula 47]

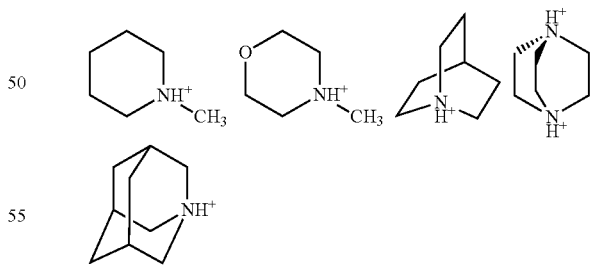

Among these, the particularly preferable are trimethylammonium ion ($Me_3NH^+$), triethylammonium ion ($Et_3NH^+$) and diisopropylethylammonium (i-$Pr_2EtNH^+$).

Then, concrete examples of R are as follows.

Examples of the linear or branched alkyl group having 1 to 10 carbon atoms include methyl group, ethyl group, n-propyl group, i-propyl group, n-butyl group, t-butyl group, n-pentyl group, n-hexyl group, n-heptyl group, n-octyl group, n-nonyl group and n-decyl group.

Examples of the alicyclic organic group having 3 to 20 carbon atoms include cyclopentyl group, cyclohexyl group, adamantyl group, norbornyl group, camphoroyl group, cyclopentylmethyl group, cyclopentylethyl group, cyclohexylmethyl group, cyclohexylethyl group, adamantylmethyl group, adamantylethyl group, norbornylmethyl group, norbornylethyl group, camphoroylmethyl group and camphoroylethyl group.

The organic group having 3 to 20 carbon atoms and containing the alicyclic organic group and the linear alkylene group means "an organic group to which one valence of the alicyclic organic group and one valence of the linear alkylene group are bonded", and concrete examples thereof include cyclopropylmethyl group, cyclobutylmethyl group, cyclopentylmethyl group, cyclohexylmethyl group, bornylmethyl group, norbornylmethyl group and adamantylmethyl group.

Examples of the monocyclic or polycyclic lactone having 3 to 30 carbon atoms are γ-butyrolactone, γ-valerolactone, angelica lactone, γ-hexylactone, γ-heptalactone, γ-octalactone, γ-nonalactone, 3-methyl-4-octanolyde (whisky lactone), γ-decalactone, γ-octalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasmine lactone, cis-jasmone lactone, methyl γ-decalactone, and the followings.

[Chemical Formula 48]

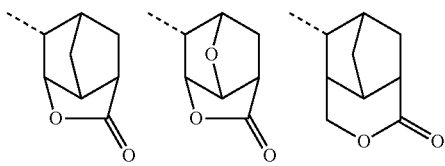

(Each dotted line represents a bonding location.)

Examples of the Aryl Group Having 6 to 20 Carbon Atoms are Phenyl group, o-tolyl group, m-tolyl group, p-tolyl group, p-hydroxyphenyl group, 1-naphthyl group, 1-naphthyl group, 1-anthracenyl group and benzyl group.

Moreover, as discussed above, some or all of hydrogen atoms in each of the alkyl group, the alicyclic organic group, the organic group having the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group having the alicyclic organic group and the linear alkylene group may be substituted with one oxygen atom to form a keto group. However, those who have in its R structure an unconjugated unsaturated moiety (a double or triple bond) are excepted.

[Sulfonic Acid Ammonium Salt]

A sulfonic acid ammonium salt of the present invention is represented by the following formula [3].

[Chemical Formula 49]

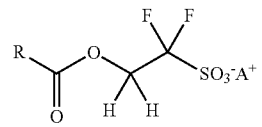

[3]

In the above formula [3], $A^+$ represents an ammonium ion. R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alicyclic organic group, the organic group having the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group having the alicyclic organic group and the linear alkylene group may be substituted with one oxygen atom to form a keto group. However, those who have in its R structure an unconjugated unsaturated moiety (a double or triple bond) are excepted.

As concrete examples of $A^+$ and concrete examples of R, those discussed in the section of the above-mentioned sulfinic acid ammonium salt represented by the formula [2] can be listed again.

Among these, triethylammonium 2-(1-adamantane)carbonyloxy-1,1-difluoroethanesulfonate represented by the following formula [14]

[Chemical Formula 50]

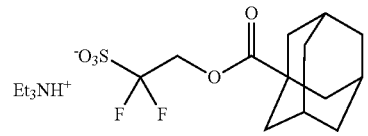

[14]

and triethylammonium 1,1-difluoro-2-(pivaloyloxy)ethanesulfonate represented by the following formula [15]

[Chemical Formula 51]

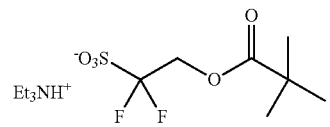

[15]

are particularly useful as a raw material for obtaining a useful photoacid generator.

[Overview of the Production Method]

Then, an invention relating to a production method will be discussed.

The present invention comprises, as represented by the following equation [7],

[Chemical Formula 52]

EQUATION [7]

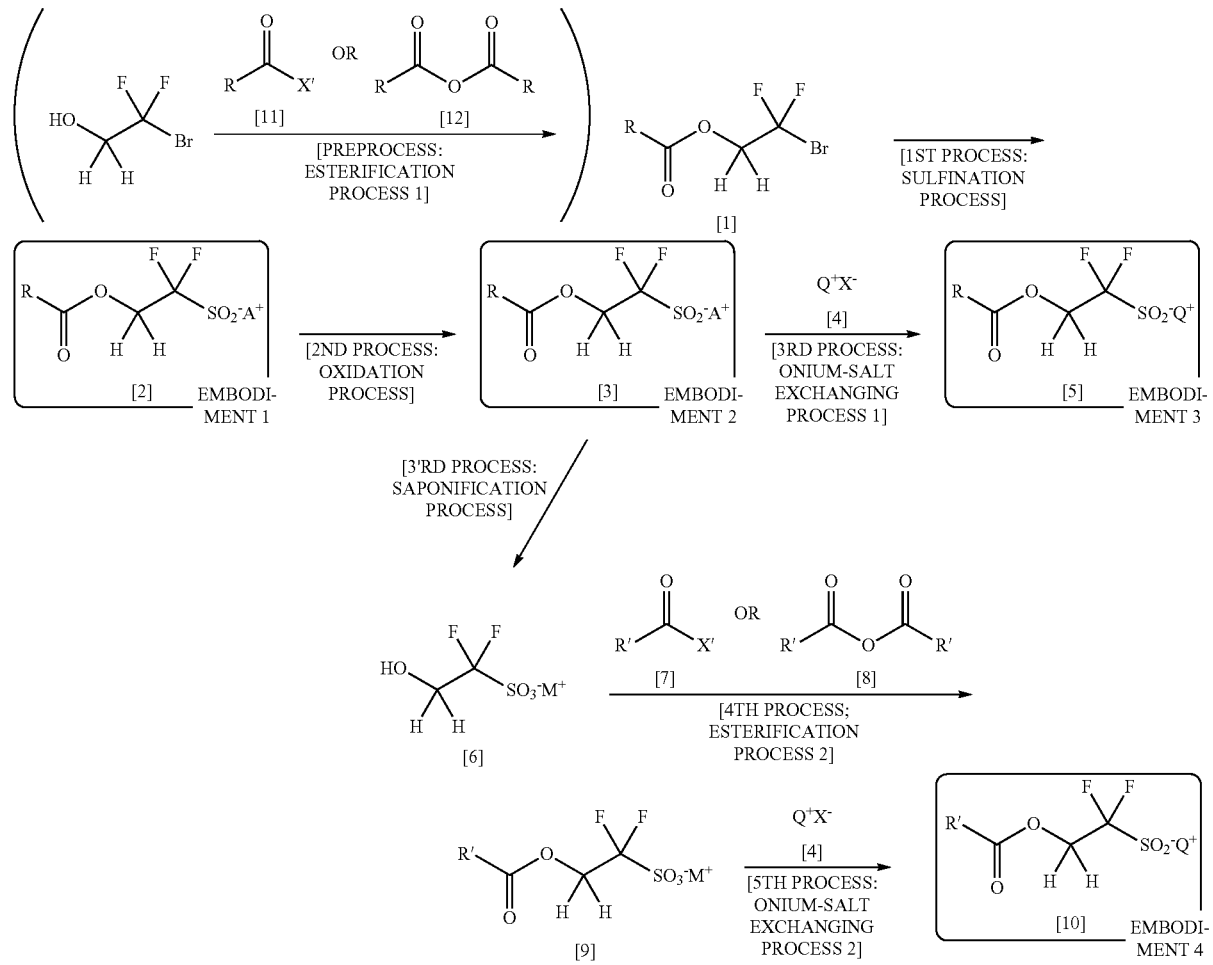

three processes consisting of: a process of reacting a carboxylic acid bromodifluoroethyl ester represented by the formula [1] with a sulfinating agent in the presence of an amine thereby obtaining a 2-alkylcarbonyloxy-1,1-difluoroethanesulfinic acid ammonium salt (a target product of the embodiment 1 of the present invention) represented by the formula [2] (The 1st process: Sulfination process); a process of reacting the obtained 2-alkylcarbonyloxy-1,1-difluoroethanesulfinic acid ammonium salt represented by the formula [2] with an oxidizing agent thereby obtaining a 2-alkylcarbonyloxy-1,1-difluoroethanesulfonic acid ammonium salt (a target product of the embodiment 2 of the present invention) represented by the formula [3] (The 2nd process: Oxidation process); and a process of carrying out an onium-salt exchange on the obtained 2-alkylcarbonyloxy-1,1-difluoroethanesulfonic acid ammonium salt represented by the formula [3] by using a monovalent onium salt represented by the formula [4], thereby obtaining a 2-alkylcarbonyloxy-1,1-difluoroethanesulfonic acid onium salt (a target product of the embodiment 3 of the present invention) represented by the formula [5] (The 3rd process: Onium-salt exchanging process 1). By passing through these processes, a 2-alkylcarbonyloxy-1,1-difluoroethanesulfonic acid onium salt having no unconjugated unsaturated moiety (a double or triple bond) as R of the formula [5] can be obtained.

Concerning those having the unconjugated unsaturated moiety (the double or triple bond), these are obtained by passing through three processes consisting of: a process of saponifying the 2-alkylcarbonyloxy-1,1-difluoroethane sulfonic acid ammonium salt represented by the formula [3] and obtained in the 2nd process thereby obtaining a 2-hydroxy-1,1-difluoroethanesulfonic acid salt represented by the formula [6] (The 3'rd process: Saponification process); a process of esterifying the obtained 2-hydroxy-1,1-difluoroethanesulfonic acid salt represented by the formula [6] thereby producing a 2-alkylcarbonyloxy-1,1-difluoroethanesulfonic acid salt represented by the formula [9] (The 4th process: Esterification process 2); and a process of carrying out an onium-salt exchange by using a monovalent onium salt represented by the formula [4] (The 5th process: Onium-salt exchanging process 2). Thus, it is also possible to obtain 2-alkylcarbonyloxy-1,1-difluoroethanesulfonic acid onium salt having the unconjugated unsaturated moiety (the double or triple bond) as R' of the formula [10].

The carboxylic acid bromodifluoroethyl ester represented by the formula [1] and serving as the starting material is readily produced by passing through a process of esterifying 2-bromo-2,2-difluoroethanol ([Preprocess]: Esterification process 1).

Hereinafter, each of the processes will be discussed in detail.

[The 1st Process: Sulfination Process]

First of all, the 1st process of the present invention will be discussed. The 1st process is a process of reacting a carboxylic acid bromodifluoroethyl ester represented by the formula [1] with a sulfinating agent in the presence of an organic base thereby obtaining a 2-alkylcarbonyloxy-1,1-difluoroethanesulfinic acid ammonium salt (Sulfination process).

As the sulfinating agent used in the present invention, it is possible to use those represented by the formula [16]

[Chemical Formula 53]

$(S^1)_m(M^1)_n \cdot pH_2O$  [16]

(In the formula [16]; $S^1$ represents $S_2O_4$, $HOCH_2SO_2$, $SO_4$ or $HSO_4$; m and n each represents an integer; p represents 0 (zero) or an integer; and $M^1$ represents Li, Na, K or $NH_4$.) Concrete examples of the sulfinating agent include lithium dithionite, sodium dithionite, potassium dithionite, ammonium dithionite, lithium hydroxymethanesulfinate, sodium hydroxymethanesulfinate, potassium hydroxymethanesulfinate, ammonium hydroxymethanesulfinate, lithium sulfite, sodium sulfite, potassium sulfite, ammonium sulfite, lithium hydrogen sulfite sodium hydrogen sulfite, potassium hydrogen sulfite and ammonium hydrogen sulfite. Among these, sodium dithionite and potassium dithionite are preferable, and sodium dithionite is particularly preferable.

The mole ratio of the sulfinating agent to the carboxylic acid bromodifluoroethyl ester [1] is normally from 0.5 to 10, preferably from 0.9 to 5.0 and particularly preferably 1.0 to 2.0.

Though this reaction can be performed in air, the sulfinating agent is sometimes decomposed by water content in air. It is, therefore, preferable to perform the reaction in a nitrogen or argon atmosphere.

A sulfination reaction using the sulfinating agent generally involves the addition of a base since the reaction can be accelerated by the addition, though sometimes develops without the base. As the base to be added, there are commonly used inorganic bases such as sodium carbonate, potassium carbonate, sodium hydrogencarbonate and potassium hydrogencarbonate; however, the present invention is characterized greatly by using an amine as the base.

The organic base used (or made coexistent) in this process is a free amine formed by removing a proton ($H^+$) from each kind of the ammonium ions exemplified as the above-mentioned $A^+$ in the formula [2]. Examples thereof are ammonia, methylamine, dimethylamine, trimethylamine, ethylamine, diethylamine, triethylamine, n-propylamine, di-n-propylamine, tri-n-propylamine, i-propylamine, di-i-propylamine, tri-i-propylamine, n-butylamine, di-n-butylamine, tri-n-butylamine, sec butylamine, di-sec-butylamine, tri-sec-butylamine, tert-butylamine, di-tert-butylamine, tri-tert-butylamine, diisopropylethylamine, phenylamine, diphenylamine, triphenylamine, and organic bases having the following structures.

[Chemical Formula 54]

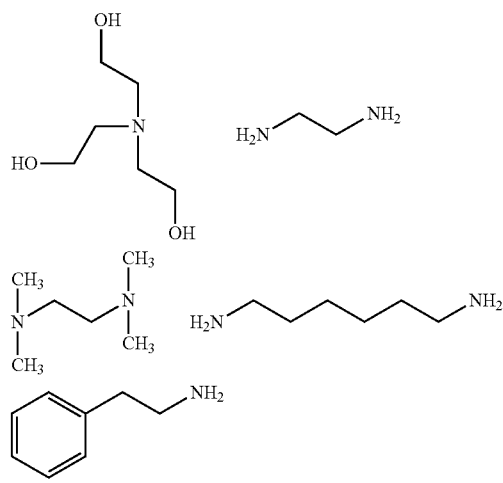

[Chemical Formula 55]

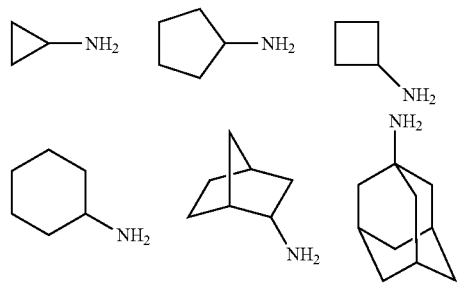

[Chemical Formula 56]

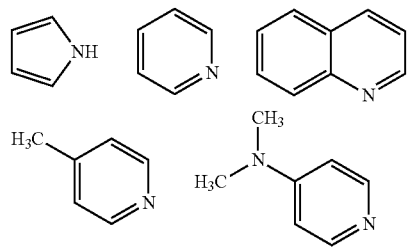

[Chemical Formula 57]

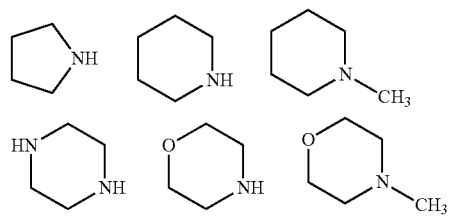

[Chemical Formula 58]

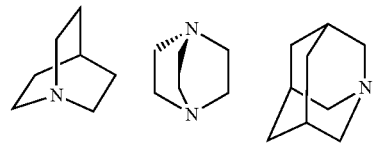

Among these, preferable examples of the organic base are trimethylamine, triethylamine, tri-n-propylamine, tri-i-propylamine, tri-n-butylamine, tri-sec-butylamine, tri-tert-butylamine, diisopropylethylamine, triphenylamine, and organic bases having the following structures.

[Chemical Formula 59]

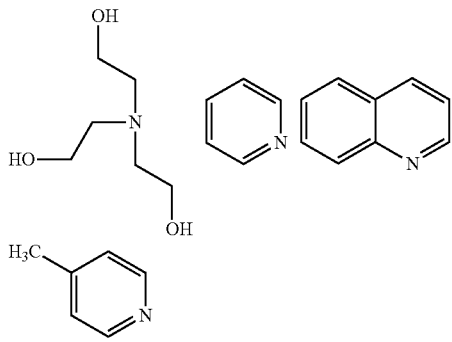

[Chemical Formula 60]

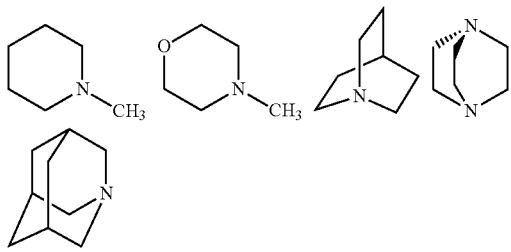

Among these, trimethylamine, triethylamine and diisopropylethylamine are particularly preferable not only because these are readily available but also because reactivity thereof in the sulfination reaction is conspicuously improved and fat-solubility of the obtained 2-alkylcarbonyloxy-1,1-difluoroethanesulfinic acid ammonium salt is sufficiently improved.

The mole ratio of the organic base to the carboxylic acid bromodifluoroethyl ester [1] is normally from 1.0 to 10.0 and preferably from 1.1 to 2.0. When the mole ratio is less than 1.0, a metal salt of 2-alkylcarbonyloxy-1,1-difluoroethanesulfinic acid is formed as a by-product by a cation derived from the sulfinating agent (e.g. a metal cation such as sodium ion, potassium ion and lithium ion). This case is not preferable not only because separation of an ammonium salt and the metal salt becomes difficult but also because the yield of the target product is reduced. A mole ratio exceeding 10.0 is not a matter of concern but not preferable also because of its economical disadvantage.

This reaction is preferably conducted in a mixture solvent of an organic solvent and water. Examples of the organic solvent are solvents having good compatibility with water, such as lower alcohols, tetrahydrofuran, N,N-dimethylformamide, N,N-dimethylacetamide, acetonitrile and dimethyl sulfoxide. The more preferable are methanol, N,N-dimethylacetamide, acetonitrile, dimethyl sulfoxide or the like. The particularly preferable is acetonitrile.

The ratio of the organic solvent to be used to 100 parts by weight of total of the organic solvent and water is normally not less than 5 parts by weight, preferably not less than 10 parts by weight, and more preferably from 20 to 90 parts by weight.

The reaction temperature is normally from 0 to 200° C. and preferably from 30 to 100° C. The reaction time is normally from 0.1 to 12 hours and preferably from 0.5 to 6 hours; however, it is preferable to determine a temporal point at which the raw material carboxylic acid bromodifluoroethyl ester [1] is consumed as the endpoint of the reaction, by using an analytical device such as thin layer chromatography (TLC) and nuclear magnetic resonance (NMR). In a case where the reaction temperature is higher than the boiling point of the organic solvent or that of water, a heat-resistant vessel such as an autoclave is used.

In comparison made with regard to the reaction time by using carboxylic acid bromodifluoroethyl esters [1] having the same structure as substrates, the reaction time when using an inorganic base such as sodium carbonate, potassium carbonate, sodium hydrogencarbonate and potassium hydrogencarbonate comes to several times to several tens times that when using the organic base. The reaction, concretely, takes about 15 to 120 hours. The reaction is not sometimes terminated. In such a case, the reaction cannot be terminated or cannot provide a high yield of the target sulfinated substance unless some operation is carried out to start the reaction again, for example, by separating a reaction solution into two layers to dump a water layer, followed by further additions of water, the sulfinating agent and the base. On the other hand, in a case of using an amine as the base, the reaction is significantly accelerated, and sometimes terminated only with several tens of minutes. Hence, it is an effect of the present invention that the reaction time can be outstandingly shortened by using an amine as the base.

Then, there will be discussed a treatment conducted after the reaction. In the 1st process of the present invention, fat-solubility of the obtained 2-alkylcarbonyloxy-1,1-difluoroethanesulfinic acid ammonium salt is improved by virtue of the use of an amine as the base. As a result, it becomes possible to extract the target sulfinic acid ammonium salt from a reaction solution (a liquid comprising water and an organic solvent having high solubility in water, or a liquid able to be separated into two layers but formed containing an organic layer in which water dissolved and a water layer in which an organic solvent is dissolved) by using an organic solvent having low or no water-solubility. Examples of such a solvent include: halogen-based solvents such as chloroform and dichloromethane; ether-based solvents such as diethyl ether, diisopropyl ether and tert-butyl methyl ether; and acetic esters such as ethyl acetate and butyl acetate.

Additionally, by rinsing the organic layer with e.g. water, inorganic substances and the like having been incorporated in the organic layer are removed therefrom. The particular problem lies within a tiny amount of fluorine ions formed in the present invention as a by-product. If it is allowed to extract ammonium salts by using the organic solvent, remaining fluorine ions can be removed by rinsing or the like (see Example 1-2, Example 2-2 and Comparative Example 1-2).

In the present reaction where bromine is to depart from the raw material carboxylic acid bromodifluoroethyl ester, residual bromine exists in the reaction solution in an amount equal to that of the raw material. If the next process (i.e., the oxidation process) is conducted while keeping the residual bromine contained, even the residual bromine is oxidized thereby generating a chemical species having the bromination ability (i.e., bromine, probably) to brominate a 2-alkylcarbonyloxy-1,1-difluoroethanesulfinic acid ammonium salt, which results in providing the raw material carboxylic acid difluoroethyl ester as the by-product. However, the residual bromine is treated by extracting the 2-alkylcarbonyloxy-1,1-difluoroethanesulfinic acid ammonium salt with a water-insoluble organic solvent and rinsing the organic solvent with an aqueous solution of sodium thiosulfate or sodium sulfite, which reached the findings that the formation of the by-product carboxylic acid bromodifluoroethyl ester in the next process (i.e., the oxidation process) can be prevented (see Example 1-3, Example 2-3, Comparative Example 2-1 and Comparative Example 2-3).

The mole ratio of sodium thiosulfate or sodium sulfite to be used to the carboxylic acid bromodifluoroethyl ester [1] is normally from 0.1 to 10.0 and preferably from 1.0 to 5.0. The concentration of the aqueous solution of sodium thiosulfate or sodium sulfite to be used is normally from 3 wt % to a saturated state but preferably from 5 to 25 wt %.

On the other hand, a 2-alkylcarbonyloxy-1,1-difluoroethanesulfinic acid metal salt obtained by using the inorganic base is low in fat-solubility and more high in water-solubility, as compared with an ammonium salt. It is therefore difficult to extract it with the organic solvent. Additionally, even if extraction is done, it is difficult to obtain the target sulfonic acid metal salt at a high yield since the metal salt is largely distributed to the water layer because of its water-solubility. Hence, condensation of the reaction solution becomes a necessity for obtaining the target sulfonic acid metal salt at a high yield. Condensation of water is generally more difficult than that of organic solvents. Moreover, if condensation is started without removing the above-mentioned trace fluorine ions formed in the present reaction as a by-product, the concentration thereof gradually increases as the condensation develops thereby resulting in corrosion of glass appliances. Furthermore, if the residual bromine is not removed, problems are raised thereby in the following processes as discussed above. Thus, another effect obtained by using the organic base in the present invention is not only that improvement of the yield enhances the fat-solubility of the sulfinated substance so as to bring about improvement of the efficiency of an isolation operation but also that inorganic impurities (e.g., fluoride ions and the residual bromine, in particular) is readily removed.

The target sulfinic acid ammonium salt is thus obtained by conducting extraction (for example, with the organic solvent), by rinsing the organic layer with water, a sodium thiosulfate aqueous solution (or a sodium sulfite aqueous solution) and the like and by distilling the solvent out of the organic layer. In some cases, purification by recrystallization process or the like may be allowed.

[The 2nd Process: Oxidation Process]

Then, the 2nd process of the present invention will be discussed. The 2nd process is a process of reacting the 2-alkylcarbonyloxy-1,1-difluoroethanesulfinic acid ammonium salt represented by the formula [2] and obtained by the 1st process with an oxidizing agent, thereby obtaining a 2-alkylcarbonyloxy-1,1-difluoroethanesulfonic acid ammonium salt represented by the formula [3] (Oxidation process).

Examples of the oxidizing agent used in this process include hydrogen peroxide, and additionally m-chloroperbenzoic acid, t-butyl hydroperoxide, potassium peroxydisulfate, potassium permanganate, sodium perborate, m-sodium iodate, chromic acid, sodium dichromate, halogen, iodobenzene dichloride, iodobenzene diacetate, osmium oxide (VIII), ruthenium oxide(VIII), sodium hypochlorite, sodium chlorite, oxide gas and ozone gas, preferably hydrogen peroxide, m-chloroperbenzoic acid and t-butyl hydroperoxide.

The mole ratio of the oxidizing agent to a 2-alkylcarbonyloxy-1,1-difluoroethanesulfinic acid salt is normally from 0.9 to 10.0 and preferably from 1.0 to 2.0. In a case where the raw material sulfinic acid ammonium salt is such a rough substance as to be unclear in exact number of moles, the oxidizing agent is added preferably relative to the molar amount of carboxylic acid bromodifluoroethyl ester represented by the formula [1].

Furthermore, the oxidizing agent can be used in combination with a transition metal catalyst. Examples of the transition metal catalyst are disodium tungstate, iron(III) chloride, ruthenium(III) chloride and selenium(IV) oxide, and preferably disodium tungstate.

The mole ratio of the transition metal catalyst to the 2-alkylcarbonyloxy-1,1-difluoroethanesulfinic acid ammonium salt is normally from 0.0001 to 1.0, preferably from 0.001 to 0.5, and more preferably from 0.001 to 0.1.

Moreover, in addition to the oxidizing agent and the transition metal catalyst, a buffer solution may be used for the purpose of adjusting the pH of the reaction solution. Examples of the buffer solution include disodium hydrogenphosphate, sodium dihydrogenphosphate, dipotassium hydrogenphosphate and potassium dihydrogenphosphate. The mole ratio of the buffer solution to the 2-alkylcarbonyloxy-1,1-difluoroethanesulfinic acid salt is normally from 0.01 to 2.0, preferably from 0.03 to 1.0 and more preferably from 0.05 to 0.5.

This reaction is usually conducted in a reaction solvent. In addition to water, also preferable examples of the reaction solvent are an organic solvent such as lower alcohols, tetrahydrofuran, N,N-dimethylformamide, N,N-dimethylacetamide, acetonitrile, dimethyl sulfoxide, acetic acid and trifluoroacetic acid. The more preferable are water, methanol, N,N-dimethylacetamide, acetonitrile and dimethyl sulfoxide. The particularly preferable are water and methanol.

Additionally, the organic solvent and water may be used in combination as necessary, in which case the ratio of the organic solvent to be used is normally not less than 5 parts by weight, preferably not less than 10 parts by weight and more preferably within a range of from 20 to 90 parts by weight relative to 100 parts by weight of total of the organic solvent and water. The amount of the reaction solvent to be used is normally from 1 to 100 parts by weight, preferably from 2 to 100 parts by weight and more preferably 5 to 50 parts by weight relative to 1 part by weight of the 2-alkylcarbonyloxy-1,1-difluoroethanesulfinic acid ammonium salt.

The reaction temperature is usually from 0 to 100° C., preferably from 5 to 60° C. and more preferably from 5 to 40° C. The reaction time is usually from 0.1 to 72 hours, preferably from 0.5 to 24 hours and more preferably from 0.5 to 12 hours; however, it is preferable that a temporal point at which the raw material 2-alkylcarbonyloxy-1,1-difluoroethanesulfinic acid ammonium salt is consumed is determined by an analytical device such as thin layer chromatography (TLC) and nuclear magnetic resonance (NMR), as the endpoint of the reaction.

Then, there will be discussed a treatment conducted after the reaction. In the above-discussed 1st process of the present invention, fat-solubility of the obtained 2-alkylcarbonyloxy-1,1-difluoroethanesulfonic acid ammonium salt is improved by virtue of the use of an amine as the base. As a result, it becomes possible to extract the target sulfonic acid ammonium salt from the reaction solution (whose main component is generally water or methanol) by using an organic solvent having low or no water-solubility. Examples of such a solvent include: halogen-based solvents such as chloroform and dichloromethane; ether-based solvents such as diethyl ether, diisopropyl ether and tert-butyl methyl ether; and acetic esters such as ethyl acetate and butyl acetate.

Additionally, by rinsing the organic layer with water or the like, water-soluble impurities including inorganic substances incorporated into the organic layer can be eliminated, with which the obtained 2-alkylcarbonyloxy-1,1-difluoroethane-sulfonic acid ammonium salt can be improved in purity (see Example 1-3, Example 2-3, Comparative Example 2-1 and Comparative Example 2-2).

The amount of water to be used in this case is normally from 1 to 100 parts by weight, preferably from 2 to 100 parts by weight, and more preferably 5 to 50 parts by weight relative to 1 part by weight of the 2-alkylcarbonyloxy-1,1-difluoroethanesulfinic acid ammonium salt.

The obtained 2-alkylcarbonyloxy-1,1-difluoroethane-sulfonic acid ammonium salt can be purified by recrystallization or the like according to circumstances.

[The 3rd Process: Onium-Salt Exchanging Process 1]

Then, the 3rd process of the present invention will be discussed. The 3rd process is a process of carrying out an onium-salt exchange on the 2-alkylcarbonyloxy-1,1-difluoroethanesulfonic acid ammonium salt represented by the formula [3] and obtained by the 2nd process, by using a monovalent onium salt represented by the formula [4]

[Chemical Formula 61]

$$Q^+X^- \quad [4],$$

, thereby obtaining a 2-alkylcarbonyloxy-1,1-difluoroethane-sulfonic acid onium salt represented by the formula [5] (Onium-salt exchanging process 1).

An Onium cation $Q^+$ included in the formula [4] is a sulfonium cation represented by the following formula (a) or the following formula (b), or an iodonium cation represented by the following formula (c).

[Chemical Formula 62]

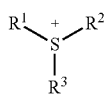

(a)

In the above formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Furthermore, any two or more of $R^1$, $R^2$ and $R^3$ may bond to each other to form a ring together with a sulfur atom shown in the formula.

[Chemical Formula 63]

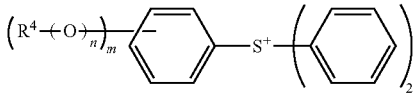

(b)

In the above formula (b): $R^4$ represents a substituted or unsubstituted linear, branched or cyclic alkyl group or alkenyl group having 1 to 20 carbon atoms or a substituted or unsubstituted aryl group having 6 to 14 carbon atoms; m represents an integer of from 1 to 5; and n represents 0 (zero) or 1.

[Chemical Formula 64]

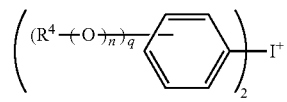

(c)

In the above formula (c): $R^4$ represents a substituted or unsubstituted linear, branched or cyclic alkyl group or alkenyl group having 1 to 20 carbon atoms or a substituted or unsubstituted aryl group having 6 to 14 carbon atoms; q represents an integer of from 0 (zero) to 5; and n represents 0 (zero) or 1.

Hereinafter, a sulfonium cation represented by the formula (a) or the formula (b) and an iodonium cation represented by the formula (c) will be discussed in detail.

Sulfonium Cation Represented by the Formula (a)

Concrete examples of $R^2$ or $R^3$ as shown in the formula (a) are as follows. Examples of alkyl group include methyl group, ethyl group, n-propyl group, isopropyl group, cyclopropyl group, n-butyl group, sec butyl group, isobutyl group, tert-butyl group, n-pentyl group, cyclopentyl group, n-hexyl group, n-heptyl group, 2-ethylhexyl group, cyclohexyl group, cycloheptyl group, 4-methylcyclohexyl group, cyclohexylmethyl group, n-octyl group, n-decyl group, 1-adamantyl group, 2-adamantyl group, bicyclo[2.2.1]hepten-2-yl group, 1-adamantanemethyl group and 2-adamantanemethyl group. Examples of alkenyl group include vinyl group, allyl group, propenyl group, butenyl group, hexenyl group and cyclohexenyl group. Examples of oxoalkyl group include 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group and 2-(4-methylcyclohexyl)-2-oxoethyl group. Examples of aryl group are: phenyl group; naphthyl group; thienyl group; alkoxy phenyl groups such as p-methoxyphenyl group, m-methoxyphenyl group, o-methoxyphenyl group, p-ethoxyphenyl group, p-tert-butoxyphenyl group and m-tert-butoxyphenyl group; alkyl phenyl group such as 2-methylphenyl group, 3-methylphenyl group, 4-methylphenyl group and ethylphenyl group; alkyl naphthyl group such as methyl naphthyl group and ethyl naphthyl group; dialkyl naphthyl group such as diethyl naphthyl group; dialkoxy naphthyl group such as dimethoxy naphthyl group and diethoxy naphthyl group. Examples of aralkyl group include benzyl group, 1-phenylethyl group and 2-phenylethyl group. Examples of aryloxoalkyl group include 2-aryl-2-oxoethyl group such as 2-phenyl-2-oxoethyl group, 2-(1-naphthyl)-2-oxoethyl group and 2-(2-naphthyl)-2-oxoethyl group. Additionally, in the case where any two or more of $R^1$, $R^2$ and $R^3$ bond to each other through a sulfur atom to form a cyclic structure, the examples include 1,4-butylene and 3-oxa-1,5-pentylene. Examples of substituent are aryl groups having a polymerizable substituent such as acryloyloxy group and methacryloyloxy group as the substituent. Concrete examples thereof include 4-(acryloyloxy)phenyl group, 4-(methacryloyloxy)phenyl group, 4-vinyloxyphenyl group and 4-vinylphenyl group.

Further concrete examples of sulfonium cation represented by the formula (a) include triphenylsulfonium, (4-tert-butylphenyl)diphenylsulfonium, bis(4-tert-butylphenyl)phenylsulfonium, tris(4-tert-butylphenynsulfonium, (3-tert-butylphenyl)diphenylsulfonium, bis(3-tert-butylphenyl) phenylsulfonium, tris(3-tert-butylphenyl)sulfonium, (3,4-ditert-butylphenyl)diphenylsulfonium, bis(3,4-ditert-butylphenyl)phenylsulfonium, tris(3,4-ditert-butylphenyl) sulfonium, (4-tert-butoxyphenyl)diphenylsulfonium, bis(4- tert-butoxyphenyl)phenylsulfonium, tris(4-tert-butoxyphenyl)sulfonium, (3-tert-butoxyphenyl)diphenylsulfonium, his (3-tert-butoxyphenyl)phenylsulfonium, tris(3-tert-butoxyphenyl)sulfonium, (3,4-ditert-butoxyphenyl)diphenylsulfonium, bis(3,4-ditert-butoxyphenyl)phenylsulfonium, tris(3,4-ditert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. More preferable examples are triphenylsulfonium, (4-tert-butylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Still further examples thereof are 4-(methacryloyloxy)phenyldiphenylsulfonium, 4-(acryloyloxy)phenyldiphenylsulfonium, 4-(methacryloyloxy)phenyldimethylsulfonium, and 4-(acryloyloxy)phenyldimethylsulfonium. Regarding these polymerizable sulfonium cation, Japanese Patent Application Publication No. 4-230645, Japanese Patent Application Publication 2005-84365 and the like can be referred to.

Sulfonium Cation Represented by the Formula (b)

In the formula (b), $R^4$—$(O)_n$— group is not particularly limited in location of $R^4$—$(O)_n$— group as a substituent, but preferably occupies position 4 or 3, more preferably position 4 of phenyl group. In the formula, n represents 0 (zero) or 1. Concrete examples of $R^4$ include methyl group, ethyl group, n-propyl group, sec-propyl group, cyclopropyl group, n-butyl group, sec butyl group, isobutyl group, tert butyl group, n-pentyl group, cyclopentyl group, n-hexyl group, cyclohexyl group, n-octyl group, n-decyl group, n-dodecyl group, 1-adamantyl group, 2-adamantyl group, bicyclo[2.2.1]hepten-2-yl group, phenyl group, 4-methoxyphenyl group, 4-tert-butylphenyl group, 4-biphenyl group, 1-naphthyl group, 2-naphthyl group, 10-anthranyl group and 2-furanyl group. In the case of n=1, the examples further include acryloyl group, methacryloyl group, vinyl group and allyl group.

Concrete examples of a sulfonium cation are (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octyl)phenyldiphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium, and (4-tert-butoxycarbonylmethyloxyphenyl)diphenylsulfonium.

Iodonium Cation Represented by the Formula (c)

In the formula (c), $R^4$—$(O)_n$— group is not particularly limited in location of $R^4$—$(O)_n$— group as a substituent, but preferably occupies position 4 or 3 of phenyl group, and more preferably occupies the position 4. In the formula, n is 0 (zero) or 1. Concrete examples of $R^4$ are the same as those discussed in the above formula (b).

Concrete examples of an iodonium cation include diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium, and (4-methacryloyloxy)phenylphenyliodonium. Among these, bis(4-tert-butylphenyl)iodonium is preferably used.

Meanwhile, examples of a monovalent anion $X^-$ shown in the formula [7] include $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonic acid anion, aromatic sulfonic acid anion, trifluoromethanesulfonic acid anion, fluorosulfonic acid anion, aliphatic carboxylic acid anion, aromatic carboxylic acid anion, fluorocarboxylic acid anion and trifluoroacetic acid anion. The preferable examples are $Cl^-$, $Br^-$, $HSO_4^-$, $BF_4^-$, aliphatic sulfonic acid ion and the like. The more preferable examples are $Cl^-$, $Br^-$ and $HSO_4^-$.

The mole ratio of the monovalent onium salt represented by the formula [4] to the 2-alkylcarbonyloxy-1,1-difluoroethanesulfonic acid ammonium salt [3] is usually from 0.5 to 10.0, preferably from 0.8 to 2.0 and more preferably from 0.9 to 1.2.

This reaction is usually conducted in a reaction solvent. Preferable examples of the reaction solvent are organic solvents such as lower alcohols, tetrahydrofuran, N,N-dimethylformamide, N,N-dimethylacetamide, acetonitrile and dimethyl sulfoxide, in addition to water. The more preferable are water, methanol, N,N-dimethylacetamide, acetonitrile and dimethyl sulfoxide. The particularly preferable is water.

Additionally, the organic solvent and water may be used in combination as necessary, in which case the ratio of the organic solvent to be used is normally not less than 5 parts by weight, preferably not less than 10 parts by weight, more preferably within a range of from 20 to 90 parts by weight relative to 100 parts by weight of total of the organic solvent and water. The amount of the reaction solvent to be used is normally from 1 to 100 parts by weight, preferably from 2 to 100 parts by weight, more preferably 5 to 50 parts by weight relative to 1 part by weight of a counter ion exchange precursor.

The reaction temperature is usually from 0 to 80° C. and preferably from 5 to 30° C. The reaction time is usually from 10 minutes to 16 hours and preferably from 30 minutes to 6 hours; however, it is preferable that a temporal point at which the raw material 2-alkylcarbonyloxy-1,1-difluoroethanesulfonic acid ammonium salt [3] is consumed is determined by an analytical device such as thin layer chromatography (TLC) and nuclear magnetic resonance (NMR), as the endpoint of the reaction.

The thus obtained 2-alkylcarbonyloxy-1,1-difluoroethanesulfonic acid onium salt represented by the formula [5] can be rinsed with an organic solvent or can be extracted to be purified. Examples of the organic solvent are preferably those who are not to be mixed with water, and therefore include esters such as ethyl acetate and n-butyl acetate, ethers such as diethyl ether, and halogenated alkyls such as methylene chloride and chloroform.

By the process as had been discussed, a 2-alkylcarbonyloxy-1,1-difluoroethanesulfonic acid onium salt not having in its structure an unconjugated unsaturated moiety (a double or triple bond) as a substituent for acyl group. This compound can be provided as a photoacid generator used to a chemically amplified resist material. Those having in its structure an unconjugated unsaturated moiety (a double or triple bond) as a substituent for acyl group are hard to be produced by the above processes so as to need the following processes to be done thereon.

[The 3'rd process: Saponification process]

Then, the 3'rd process of the present invention will be discussed. The 3'rd process is a process of saponifying the 2-alkylcarbonyloxy-1,1-difluoroethane sulfonic acid ammonium salt represented by the formula [3] and obtained by the 2nd process thereby obtaining a 2-hydroxy-1,1-difluoroethanesulfonic acid salt represented by the formula [6] (Saponification process).

A process for saponifying the 2-alkylcarbonyloxy-1,1-difluoroethanesulfonic acid ammonium salt represented by the formula [3] is not particularly limited and therefore adopted from any of commonly known saponification processes. Examples thereof are as follows.

In general, saponification reaction is conducted in the presence of a basic catalyst in which a base is exemplified by hydroxide, bicarbonate and carbonate of one or more kinds of alkali metals, ammonia and amine. Examples of alkali metal compounds are sodium hydroxide, potassium hydroxide, lithium hydroxide, sodium hydrogencarbonate, potassium hydrogencarbonate, sodium carbonate and potassium carbonate. Examples of amine are methylamine, dimethylamine, trimethylamine, ethylamine, diethylamine, triethylamine, propylamine, dipropylamine, tripropylamine, butylamine, dibutylamine, tributylamine, cyclohexylamine, benzylamine, morpholine, pyrrole, pyrrolidine, pyridine, ethanolamine, diethanolamine, triethanolamine, N,N-dimethylaminoethanol, N,N-diethylaminoethanol, ethylene diamine, diethylenetriamine, triethylenetetramine, 1,2-propylenediamine, dipropylenetriamine and tripropylenetetramine, and quaternary ammonium hydroxide salts of these.

In a case of using the same amine as that used in the 1st process (the sulfination process), a counter cation represented by $M^+$ remains an ammonium ion ($A^+$) since the raw material is an ammonium salt. However, in a case of using a base different from that used in the 1st process (the sulfination process), the counter cation represented by $M^+$ changes according to the strength of the base to be used.

The raw material 2-alkylcarbonyloxy-1,1-difluoroethanesulfonic acid ammonium salt is a salt formally comprising a difluoroalkanesulfonic acid serving as a super strong acid and an amine serving as a weak base. Accordingly, if a base stronger than the amine used in the 1st process (the sulfination process) is used in an equivalent amount to the 2-alkylcarbonyloxy-1,1-difluoroethanesulfonic acid ammonium salt of not less than 1, $M^+$ becomes a cation derived from the base used in this process. When using in an equivalent amount of not more than 1, $M^+$ becomes a mixture of a cation derived from the raw material and a cation derived from the base used in this process.

In a case of using a base weaker than the amine used in the sulfination process, the ammonium cation derived from the raw material theoretically remains unchanged either in the use of not less than 1 equivalent amount or in the use of not more than 1 equivalent amount. However, there is also an actual possibility, under the influence of compatibility between the base-derived cation used in this process and a difluoroalkanesulfonate anion, that the ammonium cation is replaced with the base-derived cation used in this process, which brings about the complexity.

Among the example bases discussed above, the preferable are sodium hydroxide, potassium hydroxide, lithium hydroxide, sodium hydrogencarbonate, potassium hydrogencarbonate, sodium carbonate and potassium carbonate included in alkali metal compounds. The particularly preferable are sodium hydroxide and potassium hydroxide included in hydroxides of alkali metals. These alkali metal hydroxides are bases stronger than amine, so that the cation to be generated (as $M^+$) is to be derived from these alkali metal hydroxides.

The mole ratio of the base to the 2-alkylcarbonyloxy-1,1-difluoroethanesulfonic acid ammonium salt [3] is usually from 0.01 to 10.0, preferably from 1.0 to 5.0 and more preferably from 1.0 to 3.0. Saponification process itself is to develop even if the mole ratio is not more than 1.0; however, if a base not identical to the base derived from the raw material ammonium salt is used in this saponification process, a hydroxyl substance is provided in the form of a mixture of various salts as discussed above. It is therefore preferable to use the base at a mole ratio of not less than 1.0.

This reaction is usually conducted in the presence of water. The mole ratio of water to the 2-alkylcarbonyloxy-1,1-difluoroethanesulfonic acid ammonium salt [3] is usually not less than 1 and has no upper limit. However, the mole ratio is preferably not more than 100 and more preferably not more than 50, since the use of an excessively large quantity of water reduces efficiency.

Additionally, water and an organic solvent can be used in combination as necessary. The organic solvent to be combined is not particularly limited, but preferably be an organic solvent who can extract the 2-hydroxy-1,1-difluoroethanesulfonic acid salt represented by the formula [6] from a water layer. Preferable examples of such an organic solvent are those who are not to be mixed with water, such as esters including ethyl acetate and n-butyl acetate, ethers including diethyl ether, and halogenated alkyls including methylene chloride and chloroform.

In this case, the amount of the organic solvent to be used is normally not less than 5 parts by weight, preferably not less than 10 parts by weight and more preferably within a range of from 20 to 90 parts by weight relative to 100 parts by weight of total of the organic solvent and water.

The reaction temperature is usually from 0 to 100° C. and preferably from 5 to 80° C. The reaction time is usually from 10 minutes to 16 hours and preferably from 30 minutes to 6 hours; however, it is preferable that a temporal point at which the raw material 2-alkylcarbonyloxy-1,1-difluoroethanesulfonic acid ammonium salt [3] is consumed is determined by an analytical device such as thin layer chromatography (TLC) and nuclear magnetic resonance (NMR), as the endpoint of the reaction.

The thus obtained 2-hydroxy-1,1-difluoroethanesulfonic acid salt represented by the formula [6] can be extracted with the organic solvent or purified by recrystallization, as necessary.

[The 4th Process: Esterification Process 2]

Then, the 4th process of the present invention will be discussed. The 4th process is a process of reacting the 2-hydroxy-1,1-difluoroethanesulfonic acid salt represented by the formula [6] and obtained by the 3'rd process with a carboxylic acid derivative represented by the formula [7] or the formula [8] to esterify it, thereby producing a 2-alkylcarbonyloxy-1,1-difluoroethanesulfonic acid ammonium salt represented by the formula [9].

In the formula [7] or the formula [8], R' represents a linear or branched alkyl group having 1 to 10 carbon atoms, a linear or branched alkenyl group of 3 to 20 carbon atoms having a polymerizable double bond at least at the end one, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms in each of the alkyl group, the alkenyl group, the alicyclic organic group, the organic group having the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alkenyl group, the alicyclic organic group, or the organic group having the alicyclic organic group and the linear alkylene group may be substituted with one oxygen atom to form a keto group. Moreover, one of hydrogen atoms on the alkyl group may be substituted with 2-acryloyloxy group or 2-methacryloyloxy group.)

Concrete examples of R' are discussed as below.

Examples of the linear or branched alkyl group having 1 to 10 carbon atoms include methyl group, ethyl group, n-propyl group, i-propyl group, n-butyl group, t-butyl group, n-pentyl group, n-hexyl group, n-heptyl group, n-octyl group, n-nonyl group and n-decyl group.

Examples of the linear or branched alkenyl group of 3 to 20 carbon atoms having a polymerizable double bond at least at the end one are vinyl group, 1-methylethenyl group, allyl group, 3-butenyl group, 1-methylallyl group, 2-methylallyl group, 4-pentenyl group and 5-hexenyl group.

Examples of the alicyclic organic group having 3 to 20 carbon atoms include cyclopentyl group, cyclohexyl group, adamantyl group, norbornyl group, camphoroyl group, cyclopentylmethyl group, cyclopentylethyl group, cyclohexylmethyl group, cyclohexylethyl group, adamantylmethyl group, adamantylethyl group, norbornylmethyl group, norbornylethyl group, camphoroylmethyl group and camphoroylethyl group.

The organic group having 3 to 20 carbon atoms and containing the alicyclic organic group and the linear alkylene group means "an organic group to which one valence of the alicyclic organic group and one valence of the linear alkylene group are bonded" and concrete examples thereof include cyclopropylmethyl group, cyclobutylmethyl group, cyclopentylmethyl group, cyclohexylmethyl group, bornylmethyl group, norbornylmethyl group and adamantylmethyl group.

Examples of the monocyclic or polycyclic lactone having 3 to 30 carbon atoms are γ-butyrolactone, γ-valerolactone, angelica lactone, γ-hexylactone, γ-heptalactone, γ-octalactone, γ-nonalactone, 3-methyl-4-octanolyde (whisky lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscaton, ε-decalactone, ε-dodecalactone, cyclohexyllactone, jasmine lactone, cis-jasmone lactone, methyl γ-decalactone, and the followings.

[Chemical Formula 65]

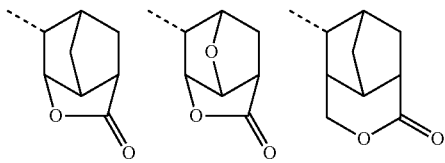

(Each Dotted Line Represents a Bonding Location.)

Examples of the aryl group having 6 to 20 carbon atoms are phenyl group, o-tolyl group, m-tolyl group, p-tolyl group, p-hydroxyphenyl group, 1-naphthyl group, 1-anthracenyl group and benzyl group.

Moreover, as discussed above, some or all of hydrogen atoms in each of the alkyl group, the alkenyl group, the alicyclic organic group, the organic group having the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms. Additionally, two hydrogen atoms on the same carbon that constructs the alkyl group, the alicyclic organic group, or the organic group having the alicyclic organic group and the linear alkylene group may be substituted with one oxygen atom to form a keto group. Furthermore, one of hydrogen atoms on the alkyl group may be substituted with 2-acryloyloxy group or 2-methacryloyloxy group.

It is possible to use an unconjugated unsaturated moiety (a double or triple bond) or an acyl group having polymerizability as discussed above, which is a great feature.

Examples of the esterification process are: a process of dehydrating and condensing a carboxylic acid represented by the formula [7] (X'=OH) and the 2-hydroxy-1,1-difluoroethanesulfonic acid salt represented by the formula [6] in the presence of an acid catalyst (Fischer esterification); and a process of reacting the 2-hydroxy-1,1-difluoroethanesulfonic acid salt represented by the formula [6] with a carboxylic acid halide (X'=Cl, Br, I, F) represented by the formula [7] or a carboxylic acid anhydride represented by the formula [8].

When using the carboxylic acid represented by the formula [7] (X'=OH), the carboxylic acid which is to act on the 2-hydroxy-1,1-difluoroethanesulfonic acid salt represented by the formula [6] is used normally in an amount ranging from 0.1 to 5 moles, preferably from 0.2 to 3 moles and more preferably from 0.5 to 2 moles relative to 1 mole of the 2-hydroxy-1,1-difluoroethanesulfonic acid salt represented by the formula [6]. It is particularly preferable to use the carboxylic acid in an amount within a range of from 0.8 to 1.5 moles.

In the reaction, an aprotic solvent such as dichloroethane, toluene, ethylbenzene, monochlorobenzene, acetonitrile and N,N-dimethylformamide is generally used. These solvents may be used singly or in combination of not less than two kinds thereof.

The reaction temperature is normally within a range of from 0 to 200° C., preferably from 20 to 180° C., and more preferably from 50 to 150° C. It is preferable to conduct the reaction while stirring.

The reaction time depends also on the reaction temperature; however, it ranges normally from several minutes to 100 hours, preferably from 30 minutes to 50 hours and more preferably from 1 to 20 hours. It is preferable that a temporal point at which the raw material 2-hydroxy-1,1-difluoroethanesulfonic acid salt [6] is consumed is determined by an analytical device such as gas chromatography (GC) and nuclear magnetic resonance (NMR), as the endpoint of the reaction.

Normally, this reaction is conducted with the addition of an organic acid such as p-toluenesulfonic acid and/or an inorganic acid such as sulfuric acid, as an acid catalyst. Additionally, 1,1'-carbonyldiimidazole, N,N-dicyclohexylcarbodiimide or the like may be added as a dehydrating agent. The amount of the acid catalyst to be used is not particularly limited but preferably within a range of from 0.0001 to 10 moles, preferably from 0.001 to 5 moles and more preferably from 0.01 to 1.5 moles relative to 1 mole of the 2-hydroxy-1,1-difluoroethanesulfonic acid salt [6].

It is preferable to conduct esterification reaction using the acid catalyst while carrying out dehydration, for example, by using Dean-Stark apparatus, since the reaction time tends to be shortened.

By taking normal means such as extraction, distillation, recrystallization and the like after the termination of the reaction, a 2-alkylcarbonyloxy-1,1-difluoroethane sulfonic acid ammonium salt represented by the formula [9] can be obtained. Moreover, purification thereof by using column chromatography, recrystallization or the like is acceptable as necessary.

On the other hand, in the case of using the carboxylic acid halide (X'=Cl, Br, I, F) represented by the formula [7] or the carboxylic acid anhydride represented by the formula [8], the amount of the carboxylic acid halide represented by the formula [7] or the carboxylic acid anhydride represented by the formula [8] to be used and made act on the 2-hydroxy-1,1-difluoroethanesulfonic acid salt [6] is not particularly limited; however, it ranges normally from 0.1 to 5 moles, preferably from 0.2 to 3 moles and more preferably from 0.5 to 2 moles relative to 1 mole of the 2-hydroxy-1,1-difluoroethanesulfonic acid salt [6]. It is particularly preferable to use the carboxylic acid halide or the carboxylic acid anhydride in an amount ranging from 0.8 to 1.5 moles.

The reaction may be conducted in the absence of solvents or may be conducted in a non-reactive solvent. Such solvents are required only to be non-reactive and therefore not particularly limited. However, hydrocarbon-based nonpolar solvents such as n-hexane, benzene and toluene are not preferable as the solvent used in this process, since the 2-hydroxy-1,1-difluoroethanesulfonic acid salt [6] is hardly dissolved in these solvents. The preferable examples are: water; ketone-based solvents such as acetone, methyl ethyl ketone and methyl isobutyl ketone; ester-based solvents such as ethyl acetate and butyl acetate; ether-based solvents such as diethyl ether, diethylene glycol dimethyl ether, tetrahydrofuran and dioxane; halogen-based solvents such as dichloromethane, chloroform, carbon tetrachloride, 1,2-dichloroethane, tetrachloroethylene, chlorobenzene and ortho-chlorobenzene; and polar solvents such as acetonitrile, N,N-dimethylformamide, N,N-dimethylimidazolidinone, dimethylsulfoxide and sulfolane. These solvents may be used singly or in combination of not less than two kinds thereof.

The reaction temperature is not particularly limited and normally within a range of from −78 to 150° C., preferably from −20 to 120° C. and more preferably from 0 to 100° C.

The reaction time depends also on the reaction temperature; however, it ranges normally from several minutes to 100 hours, preferably from 30 minutes to 50 hours and more preferably from 1 to 20 hours. It is preferable that a temporal point at which the raw material 2-hydroxy-1,1-difluoroethanesulfonic acid salt [6] is consumed is determined by an analytical device such as nuclear magnetic resonance (NMR), as the endpoint of the reaction.

In the case of using the carboxylic acid halide represented by the formula [7], it may be allowed to conduct the reaction in the absence of catalysts while removing a product hydrogen halide (e.g. hydrogen chloride) from the reaction system, or in the use of a dehydrohalogenating agent (an acid acceptor). Additionally, in the case of using the carboxylic acid anhydride [8], the acid acceptor for receiving by-product acids may be used.

Examples of the acid acceptor include: organic bases such as triethylamine, pyridine, picoline, dimethylaniline, diethylaniline, 1,4-diazabicyclo[2.2.2]octane (DABCO) and 1,8-diazabicyclo[5.4.0]undec-7-ene (DBU); and inorganic bases such as sodium hydrogencarbonate, sodium carbonate, potassium carbonate, lithium carbonate, sodium hydroxide, potassium hydroxide, calcium hydroxide and magnesium oxide. The amount of the acid acceptor to be used is not particularly limited but ranges from 0.05 to 10 moles, preferably from 0.1 to 5 moles and more preferably from 0.5 to 3 moles relative to 1 mole of the 2-hydroxy-1,1-difluoroethanesulfonic acid salt [6].

By taking normal means such as extraction and recrystallization after the termination of the reaction, the 2-alkylcarbonyloxy-1,1-difluoroethane sulfonic acid ammonium salt represented by the formula [9] can be obtained. Moreover, purification thereof by using column chromatography, recrystallization or the like is acceptable as necessary.

[The 5th Process: Onium-Salt Exchanging Process 2]

Then, the 5th process of the present invention will be discussed. The 5th process is a process of carrying out an onium-salt exchange by using the monovalent onium salt represented by the formula [4] on the 2-alkylcarbonyloxy-1,1-difluoroethanesulfonic acid ammonium salt represented by the formula [9] and obtained by the 4th process, thereby obtaining a 2-alkylcarbonyloxy-1,1-difluoroethanesulfonic acid onium salt represented by the formula [10] (Onium-salt exchanging process 2). This process can be performed in the same manner as the above-mentioned 3rd process (Onium-salt exchanging process 1).

By the way, the 4th process and the 5th process can be replaced with each other in order (Equation [17]).

[Chemical Formula 66]

EQUATION [8]

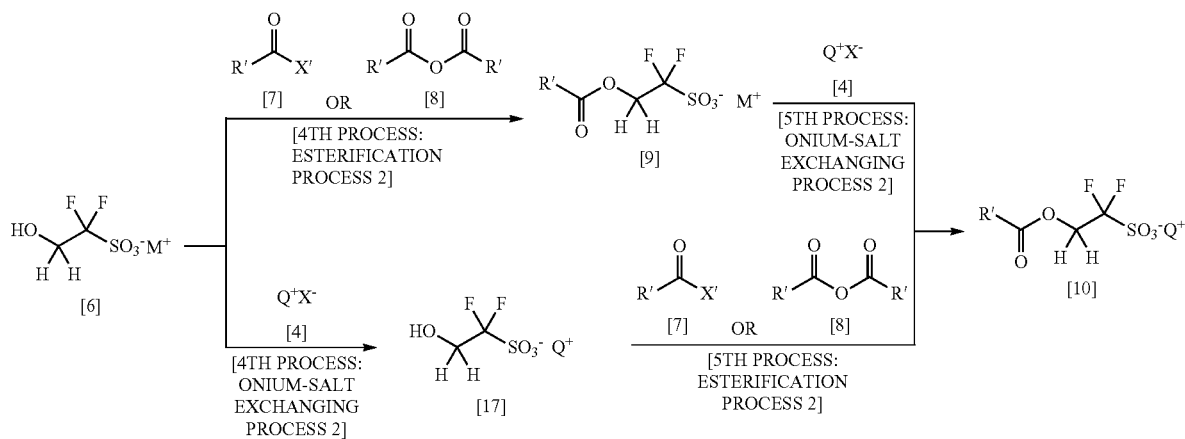

Namely, it is a process for carrying out an onium-salt exchange by using the monovalent onium salt represented by the formula [4] on the 2-hydroxy-1,1-difluoroethanesulfonic acid salt [6] to obtain a 2-hydroxy-1,1-difluoroethanesulfonic acid onium salt represented by the formula [17] (The 4'th process: Onium-salt exchanging process 2), followed by esterification thereof, thereby producing a 2-alkylcarbonyloxy-1,1-difluoroethanesulfonic acid onium salt represented by the formula [10] (The 5'th process: Esterification process 2).

This process, however, requires to use an enormously excessive amount of onium salt in the 4'th process (Onium-salt exchanging process 2), and additionally brings about some disadvantages such as difficulty in purifying the 2-alkylcarbonyloxy-1,1-difluoroethanesulfonic acid onium salt represented by the formula [10] and obtained upon the 5'th process (see Comparative Example 4$^{-1}$ and Comparative Example 4-2).

Accordingly, it is a preferable process to conduct the 4th process and the 5th process of the present invention in this order, as discussed above.

Finally, a preprocess of the present invention will be discussed. The preprocess is a process of reacting 2-bromo-2,2-difluoroethanol with a carboxylic acid derivative represented by the formula [11] or the formula [12] to esterify it, thereby producing the carboxylic acid bromodifluoroethyl ester represented by the formula [1].

In this process, the same process as the 4th process is adopted with the exceptions of using a carboxylic acid or a carboxylic acid halide represented by the formula [11] instead of the carboxylic acid or the carboxylic acid halide represented by the formula [7] and of using a carboxylic anhydride represented by the formula [12] instead of the carboxylic anhydride represented by the formula [8]. With this, it becomes possible to produce the carboxylic acid bromodifluoroethyl ester represented by the formula [1] from 2-bromo-2,2-difluoroethanol.

The present invention will be more specifically discussed with reference to the following Examples; however, the present invention is not limited by these Examples.

EXAMPLE 1-1

Production of (2'-Bromo-2',2'-difluoro)ethyl 1-adamantanecarboxylate(Preprocess; Esterification process 1)

[Chemical Formula 67]

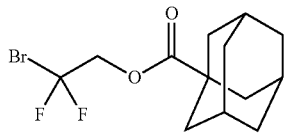

A 300 mL reactor was charged, under nitrogen, with 14.2 g (71.3 millimoles) of 1-adamantanecarbonyl chloride and 120 mL of THF (脱水溶媒グレード), followed by putting it in an iced bath. There, 16.1 g (92% purity, 91.8 millimoles/1.29 equivalents) of 2-bromo-2,2-difluoroethanol was added, and 10.1 g (99.8 millimoles/1.4 equivalents) of triethylamine was added dropwise. After the dropping, stirring was conducted at 60° C. for 23 hours. Then, 50 mL of water was added thereto, and extraction was conducted two times with 150 mL of diisopropyl ether. The obtained organic layer was further rinsed with diluted hydrochloric acid, sodium bicarbonate water and brine, followed by removing water content with sodium sulfate, filtration, and then distilling isopropyl ether off, thereby obtaining 23.2 g of the target 2'-bromo-2',2'-difluoroethyl 1-adamantanecarboxylate. In this case, the purity was 85% and the yield was 86%.

Properties of (2'-Bromo-2',2'-difluoro)ethyl 1-adamantanecarboxylate $^1$H NMR (Solvent for measurement: Deuterated chloroform, Reference material: Tetramethylsilane); δ=4.51 (t, J=11.6 Hz, 2H; CH$_2$), 1.97 (m, 3H; 1-Ad), 1.87 (m, 6H; 1-Ad), 1.66 (m, 6H; 1-Ad).

$^{19}$F NMR (Solvent for measurement: Deuterated chloroform, Reference material: Trichlorofluoromethane); δ=−56.46 (t, J=11.6 Hz, 2F; CF$_2$).

EXAMPLE 1-2

Production of Triethylammonium 2-(1-adamantane)carbonyloxy-1,1-difluoroethanesulfinate

[Chemical Formula 68]

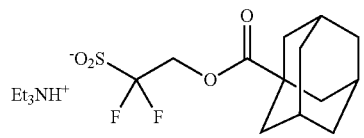

A 200 mL reactor was charged with 18.0 g (97% purity, 54.0 millimoles) of (2'-bromo-2',2'-difluoro)ethyl 1-adamantanecarboxylate, 50 g of acetonitrile, 40 g of water, 15.0 g (86.4 millimoles/1.6 equivalents) of sodium dithionite and 9.8 g (97.2 millimoles/1.8 equivalents) of triethylamine in this order, followed by stirring for 1 hour at room temperature. A reaction liquid was separated into an organic layer and a water layer. The organic layer was subjected to the distillation of acetonitrile and the addition of 40 mL of dichloromethane, thereby obtaining a dichloromethane solution. The water layer was extracted with 20 mL of dichloromethane and then mixed with the organic layer. The obtained organic layer was rinsed with 10% sodium thiosulfate aqueous solution, water and brine, followed by distilling dichloromethane out thereof, thereby obtaining 23.2 g of the target triethylammonium 241 adamantane)carbonyloxy-1,1-difluoroethanesulfinate. In this case, the purity was 82% and the yield was 86%.

Properties of Triethylammonium 2-(1-adamantane) carbonyloxy-1,1-difluoroethanesulfinate $^1$H NMR (Solvent for measurement: Deuterated dimethyl sulfoxide, Reference material; Tetramethylsilane); δ=4.41 (t, J=16.0 Hz, 2H; CH$_2$), 3.05 (q, J=7.2 Hz, 6H; Et$_3$N), 1.94 (m, 3H; 1-Ad), 1.81 (m, 6H; 1-Ad), 1.64 (m, 6H; 1-Ad), 1.18 (t, J=7.2 Hz, 9H; Et$_3$N).

$^{19}$F NMR (Solvent for measurement; Deuterated dimethyl sulfoxide, Reference material: Trichlorofluoromethane); δ=−120.41 (t, J=16.0 Hz, 2F; CF$_2$).

EXAMPLE 1-3

Production of Triethylammonium 2-(1-adamantane) carbonyloxy-1,1-difluoroethanesulfonate (The 2nd Process: Oxidation Process)

[Chemical Formula 69]

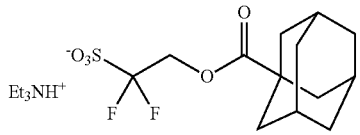

A 200 mL reactor was charged with 23.2 g (82% purity, 46.4 millimoles) of triethylammonium 2-(1-adamantane)carbonyloxy-1,1-difluoroethanesulfinate obtained by Example 1-2, 100 mL of water, 0.023 g (0.070 millimole/0.0015 equivalent) of disodium tungstate dihydrate and 7.4 g (65.0 millimoles/1.4 equivalents) of 30% hydrogen peroxide solution, followed by stirring for 3 hours at room temperature. Thereafter, this reaction solution was checked by using $^{19}$F NMR, with which it was confirmed that triethylammonium 2-(1-adamantane)carbonyloxy-1,1-difluoroethane sulfinate was completely consumed and that (2'-bromo-2',2'-difluoro)ethyl 1-adamantanecarboxylate formed as a by-product was less than 1%. The reaction solution was extracted with 40 mL of dichloromethane two times, and then a solvent was distilled out of the obtained organic layer, followed by drying the obtained solid. The solid was dissolved in methanol and then an insoluble residue was separated off by filtration, thereby obtaining a methanol solution. The obtained methanol solution was added dropwise to isopropyl ether, followed by stirring for 1 hour at room temperature. Upon this, a precipitated solid was separated by filtration and dried, thereby obtaining 17.3 g of the target triethylammonium 2-(1-adamantane)carbonyloxy-1,1-difluoroethanesulfonate. In this case, the purity was 97% and the yield was 85%.

Properties of Triethylammonium 2-(1-adamantane) carbonyloxy-1,1-difluoroethanesulfonate $^1$H NMR (Solvent for measurement: Deuterated dimethyl sulfoxide, Reference material: Tetramethylsilane); δ=4.52 (t, J=15.6 Hz, 2H; CH$_2$), 3.09 (q, J=7.2 Hz, 6H; Et$_3$N), 1.95 (m, 31-I; 1-Ad), 1.82 (m, 6l-1; 1-Ad), 1.65 (m, 6H; 1-Ad), 1.17 (t, J=7.2 Hz, 9H; Et$_3$N).

$^{19}$F NMR (Solvent for measurement: Deuterated dimethyl sulfoxide, Reference material: Trichlorofluoromethane); δ=−113.98 (t, J=15.6 Hz, 2F; CF$_2$).

EXAMPLE 1-4

Production of Triphenylsulfonium 2-(1-adamantane) carbonyloxy-1,1-difluoroethanesulfonate

[Chemical Formula 70]

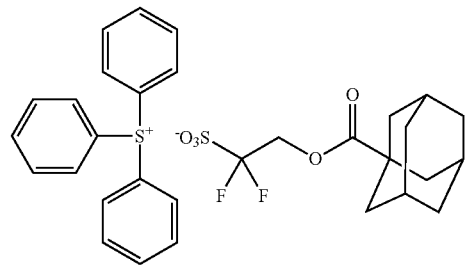

A 500 mL reactor was charged with 15.0 g (97% purity, 34.2 millimoles) of triethylammonium 2-(1-adamantane)carbonyloxy-1,1-difluoroethanesulfonate obtained by Example 1-3 and 150 g of water, followed by adding dropwise an aqueous solution of triphenylsulfonium bromide [12.9 g (37.6 millimoles/1.1 equivalents) of triphenylsulfonium bromide and 150 g of water] at room temperature. Then, stirring was conducted at room temperature for 2 hours, followed by filtration and drying solid, thereby obtaining 18.4 g of the target triphenylsulfonium 2-(1-adamantane)carbonyloxy-1,1-difluoroethanesulfonate. In this case, the purity was 98% and the yield was 90%.

Properties of Triphenylsulfonium 2-(1-adamantane) carbonyloxy-1,1-difluoroethanesulfonate $^1$H NMR (Solvent for measurement: Deuterated dimethyl sulfoxide, Reference material: Tetramethylsilane); δ=7.91−7.72 (m, 15H, Ph$_3$S$^+$), 4.51 (t, J=15.3 Hz, 2H; CH$_2$), 1.96 (m, 3H; 1-Ad), 1.82 (m, 6H; 1-Ad), 1.65 (m, 6H; 1-Ad).

$^{19}$F NMR (Solvent for measurement: Deuterated dimethyl sulfoxide, Reference material: Trichlorofluoromethane); δ=−113.97 (t, J=15.3 Hz, 2F; CF$_2$).

EXAMPLE 2-1

Production of 2-Bromo-2,2-difluoroethyl pivalate (Preprocess: Esterification Process 1)

[Chemical Formula 71]

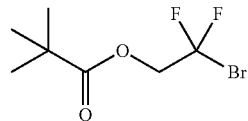

A glass flask equipped with a thermometer, a condenser and a dropping funnel was charged with 271 g (2.24 moles) of pivaloyl chloride, 360 g (2.23 moles) of 2-bromo-2,2-difluoroethanol and 1.5 L of diisopropyl ether, followed by stirring.

Then, 318 g (3.14 moles) of triethylamine was added dropwise thereto, in an iced bath. After the termination of the dropping, stirring was conducted for 1 hour at room temperature. Then, the termination of the reaction was confirmed by gas chromatography. With the addition of 300 mL of water, a reaction solution was completely dissolved therein, followed by adding 500 mL of 2N hydrochloric acid thereto. The reaction solution was separated into an organic layer and a water layer, followed by extracting the water layer with 500 ml of diisopropyl ether. Subsequently, the organic layer was rinsed with 500 ml of saturated brine, followed by drying with anhydrous sodium sulfate. Thereafter, a solvent was distilled off, thereby obtaining 485 g (82% yield, 93% purity) of 2-bromo-2,2-difluoroethyl pivalate in the form of a light yellow liquid.

Properties of 2-Bromo-2,2-difluoroethyl pivalate $^1$H NMR (Solvent for measurement: Deuterated chloroform, Reference material: Tetramethylsilane); δ=4.52 (t, 2H), 1.19 (s, 9H).

$^{19}$F NMR (Solvent for measurement: Deuterated chloroform, Reference material: Trichlorofluoromethane); δ=−56.6 (t, 2F).

EXAMPLE 2-2

Production of Triethylammonium 1,1-difluoro-2-(pivaloyloxy)ethanesulfinate (The 1st Process: Sulfination Process)

[Chemical Formula 72]

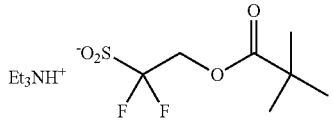

A 1 L vessel was charged with 96.8 g (93% purity, 367.2 millimoles) of 2-bromo-2,2-difluoroethyl pivalate, 200 g of acetonitrile, 250 g of water, 95.8 g (550.8 millimoles/1.5 equivalents) of sodium dithionite and 83.0 g (550.8 millimoles/1.5 equivalents) of triethylamine in this order, followed by stirring for 2 hours at room temperature. A reaction liquid was separated into an organic layer and a water layer. The organic layer was subjected to the distillation of acetonitrile and the addition of 100 mL of dichloromethane, thereby obtaining a dichloromethane solution. The water layer was extracted with 50 mL of dichloromethane and then mixed with the organic layer. The obtained organic layer was rinsed with 10% sodium thiosulfate aqueous solution, water and brine, followed by distilling dichloromethane off, thereby obtaining 111.4 g of the target triethylammonium 2-pivaloyloxy-1,1-difluoroethanesulfate at a purity of 76% and a yield of 83%.

Properties of Triethylammonium 1,1-difluoro-2-(pivaloyloxy)ethanesulfinate $^1$H NMR (Solvent for measurement: Deuterated chloroform, Reference material: Tetramethylsilane); δ=4.43 (t, 2H), 3.04 (q, 6H), 1.17 (t, 9H), 1.11 (s, 9H).

$^{19}$F NMR (Solvent for measurement: Deuterated chloroform, Reference material: Trichlorofluoromethane); δ=−120.3 (t, 3F).

EXAMPLE 2-3

Production of Triethylammonium 1,1-difluoro-2-(pivaloyloxy)ethanesulfonate (The 2nd Process: Oxidation Process)

[Chemical Formula 73]

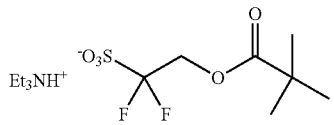

A 500 mL vessel was charged with 111.4 g (83% purity, 279.1 millimoles) of the triethylammonium 1,1-difluoro-2-(pivaloyloxy)ethanesulfinate obtained by Example 2-2, 100 mL of water, and 40.0 g (334.9 millimoles/1.2 equivalents) of 30% hydrogen peroxide solution, followed by stirring for 3 hours at room temperature. Thereafter, this reaction solution was checked by using $^{19}$F NMR, with which it was confirmed that 1,1-difluoro-2-(pivaloyloxy)ethanesulfate was completely consumed and that 2-bromo-2,2-difluoroethyl pivalate formed as a by-product was less than 1%. The reaction solution was extracted with 200 mL of dichloromethane two times, and then a solvent was distilled out of the obtained organic layer, followed by drying the obtained solid. The solid was dissolved in methanol and then an insoluble residue was separated off by filtration, thereby obtaining a methanol solution. The obtained methanol solution was added dropwise to isopropyl ether, followed by stirring for 1 hour at room temperature. Upon this, a precipitated solid was separated by filtration and dried, thereby obtaining 86.8 g of triethylammonium 1,1-difluoro-2-(pivaloyloxy)ethanesulfonate at a purity of 85% and a yield of 95%.

Properties of Triethylammonium 1,1-difluoro-2-(pivaloyloxy)ethanesulfonate $^1$H NMR (Solvent for measurement: Deuterated dimethyl sulfoxide, Reference material: Tetramethylsilane); δ=4.52 (t, 2H), 3.06 (q, 6H), 1.18 (t, 9H), 1.14 (s, 9H).

$^{19}$F NMR (Solvent for measurement: Deuterated chloroform, Reference material: Trichlorofluoromethane); δ=−113.9 (t, 3F).

EXAMPLE 2-4

Production of Sodium 2-hydroxy-1,1-difluoroethanesulfonic acid (The 3'rd Process: Saponification Process)

[Chemical Formula 74]

A 2 L reactor was charged with 146.3 g (95% purity, 0.40 mole) of triethylammonium 1,1-difluoro-2-(pivaloyloxy) ethanesulfonate obtained by Example 2-3, 500 mL of water and 100 g (1.2 moles/3 equivalents) of 48% sodium hydroxide aqueous solution, followed by stirring for 2 hours at room temperature. Thereafter, 150 g (1.52 moles/3.8 equivalents) of 37% hydrochloric acid aqueous solution was added thereto, followed by stirring for 1 hour at room temperature. It was rinsed with 250 mL of diisopropyl ether two times and then a solvent was distilled out of the obtained water layer, thereby obtaining 72.2 g of the target sodium 2-hydroxy-1,1-difluoroethanesulfonic acid. In this case, the purity was 71% and the yield was 98%.

Properties of Sodium 2-hydroxy-1,1-difluoroethanesulfonic acid $^1$H NMR (Solvent for measurement: Deuterated dimethyl sulfoxide, Reference material: Tetramethylsilane); δ=3.80 (t, J=16.0 Hz, 2H; CH$_2$).

$^{19}$F NMR (Solvent for measurement: Deuterated dimethyl sulfoxide, Reference material: Trichlorofluoromethane); δ=−115.34 (t, J=16.0 Hz, 2F; CF$_2$).

EXAMPLE 2-5

Production of Sodium 1,1-difluoro-2-(2-methacryloyloxy)-ethanesulfonic acid (The 4th Process: Esterification Process 2)

[Chemical Formula 75]

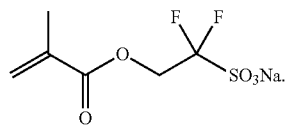

[Chemical Formula 75]

A 10 L reactor was charged with 295 g (75% purity, 1.2 moles) of sodium 2-hydroxy-1,1-difluoroethanesulfonic acid obtained by the same process as Example 2-4, 3 kg of acetonitrile, 40 mg of nonflex MBP and 367.0 g (2.4 moles/2.0 equivalents) of methacrylic anhydride in this order, followed by putting it into an iced bath. There, 370 g (3.6 moles/3.0 equivalents) of triethylamine was added dropwise. After the dropping, stirring was conducted at room temperature for 5 hours. Thereafter, 1.5 L of water was added and then acetonitrile was distilled off. The obtained water layer was rinsed with 0.5 L of isopropyl ether two times, thereby obtaining 285.2 g of the target sodium 1,1-difluoro-2-(2-methacryloyloxy)-ethanesulfonic acid (10 wt % aqueous solution). In this case, the yield was 95%.

Properties of Sodium 1,1-difluoro-2-(2-methacryloyloxy)-ethanesulfonic acid $^1$H NMR (Solvent for measurement: Deuterated dimethyl sulfoxide, Reference material: Tetramethylsilane); δ=5.91 (s, 1H), 5.52 (s, 1H), 4.61 (t, J=16.0 Hz, 2H; CH$_2$), 1.81 (s, 3H).

$^{19}$F NMR (Solvent for measurement: Deuterated dimethyl sulfoxide, Reference material: Trichlorofluoromethane); δ=−113.68 (t, J=16.0 Hz, 2F; CF$_2$).

EXAMPLE 2-6

Production of Triphenylsulfonium 1,1-difluoro-2-(2-methacryloyloxy)-ethanesulfonic acid (The 5th Process: Onium-Salt Exchanging Process 2)

[Chemical Formula 76]

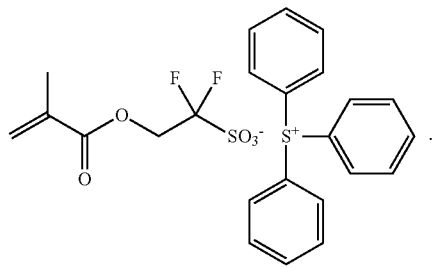

[Chemical Formula 76]

A 5 L reactor was charged with 288.0 g of sodium 1,1-difluoro-2-(2-methacryloyloxy)-ethanesulfonic acid (10 wt % aqueous solution) obtained by Example 2-5, 0.8 kg of chloroform and 40 mg of nonflex MBP. There, an aqueous solution of triphenylsulfonium chloride [409 g (1.37 moles/1.2 equivalents) of triphenylsulfonium chloride and 800 g of water] was added dropwise at room temperature, followed by stirring at room temperature for 1.5 hours. Thereafter it was separated into a water layer and a chloroform layer. The obtained chloroform layer was rinsed one time with 2N HCl and six times with water, followed by distilling chloroform off. There, 1.1 kg of methyl ethyl ketone and 0.3 kg of hexane were added, followed by filtration and preparing a methyl ethyl ketone/hexane mixture solution. On the other hand, a 5 L reactor charged with 2 L of hexane was prepared, to which the prepared methyl ethyl ketone/hexane mixture solution was added dropwise at room temperature while stirring. After the dropping, stirring was conducted at room temperature for 1 hour. The precipitated solid was separated by filtration and then dried, thereby obtaining 562 g of the target triphenylsulfonium 1,1-difluoro-2-(2-methacryloyloxy)-ethanesulfonate. In this case, the purity was 98% and the yield was 98%.

Properties of Triphenylsulfonium 1,1-difluoro-2-(2-methacryloyloxy)-ethanesulfonate $^1$H NMR (Solvent for measurement: Deuterated dimethyl sulfoxide, Reference material: Tetramethylsilane); δ=7.92−7.65 (m, 15H, Ph$_3$S$^+$), 6.19 (s, 1H), 5.57 (s, 1H), 4.81 (t, J=16.0 Hz, 2H; CH$_2$), 1.92 (s, 3H).

$^{19}$F NMR (Solvent for measurement: Deuterated dimethyl sulfoxide, Reference material: Trichlorofluoromethane); δ=−114.49 (t, J=16.0 Hz, 2F; CF$_2$).

COMPARATIVE EXAMPLE 1-1

Production of Sodium 2-(1-adamantane)carbonyloxy-1,1-difluoroethanesulfinic acid (The 1st Process: Sulfination Process)

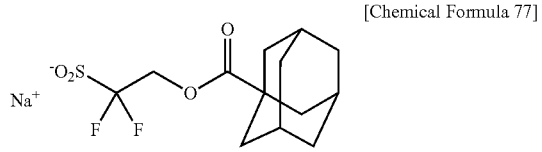

[Chemical Formula 77]

A 300 mL vessel was charged, under nitrogen, with 22.8 g (85% purity, 60.0 of (2'-bromo-2',2'-difluoro)ethyl 1-adamantanecarboxylate, 80 g of acetonitrile, 10.1 g (120.0 millimoles/2.0 equivalents) of sodium hydrogencarbonate, 15.7 g (90.0 millimoles/1.5 equivalents) of sodium dithionite and 40 g of water, followed by stirring at 70° C. for 66 hours. The vessel was further charged with 6.7 g (80.0 millimoles) of sodium hydrogencarbonate and 10.5 g (60.0 millimoles) of sodium dithionite, followed by stirring at 80° C. for 24 hours. Extraction was conducted on a reaction solution with 30 mL of acetonitrile one time and then a solvent was distilled out of the obtained organic layer, followed by rinsing with 400 mL of diisopropyl ether. Then, filtration was conducted thereon, followed by drying a solid, thereby obtaining 12.0 g of the target sodium 2-(1-adamantane)carbonyloxy-1,1-difluoroethanesulfinic acid. In this case, the yield was 39% and the purity was 65%. Additionally, a solvent was distilled out of a rinsing liquid thereby recovering 11.3 g of (2'-bromo-2',2'-difluoro)ethyl 1-adamantanecarboxylate. In this case, the purity was 71%.

A 200 mL vessel was charged, under nitrogen, with 11.1 g (71% purity, 24.4 millimoles) of the recovered (2'-bromo-2',2'-difluoro)ethyl 1-adamantanecarboxylate, 40 g of acetonitrile, 4.1 g (48.8 millimoles/2.0 equivalents) of sodium hydrogencarbonate, 6.4 g (36.6 millimoles/1.5 equivalents) of sodium dithionite and 40 g of water, followed by stirring at 80° C. for 18 hours. The vessel was further charged with 1.9 g (22.4 millimoles) of sodium hydrogencarbonate and 2.9 g (16.8 millimoles) of sodium dithionite, followed by stirring at 80° C. for 22 hours. Extraction was conducted on a reaction solution with 30 mL of acetonitrile one time and then a solvent was distilled out of the obtained organic layer, followed by rinsing with 250 mL of diisopropyl ether. Then, filtration was conducted thereon, followed by drying a solid, thereby obtaining 6.9 g of the target sodium 2-(1-adamantane)carbonyloxy-1,1-difluoroethanesulfinic acid. In this case, the yield was 21% and the purity was 61%.

If sodium hydrogencarbonate was used as a base as discussed above, not only the reaction time is long but also the reaction cannot be finished.

COMPARATIVE EXAMPLE 1-2

Production of sodium 1,1-difluoro-2-(pivaloyloxy)ethanesulfinic acid (The 1St Process: Sulfination Process)

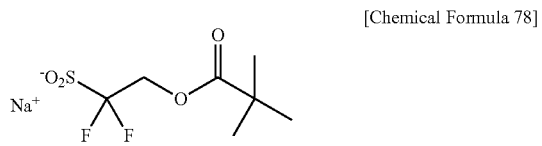

[Chemical Formula 78]

A glass flask equipped with a thermometer and a condenser was charged with 376 g (1.24 moles) of 2-bromo-2,2-difluoroethyl pivalate of 81% purity, 154 g (1.83 moles) of sodium hydrogencarbonate, 319 g (1.83 moles) of sodium dithionite, 1.2 L of acetonitrile and 1.2 L of water, followed by stirring for 4 hours at 70° C. It was cooled to room temperature and a water layer was eliminated therefrom. Thereafter 154 g (1.83 moles) of sodium hydrogencarbonate, 319 g (1.83 moles) of sodium dithionite and 1.2 L of water were added thereto, followed by stirring for 4 hours at 70° C. This operation was repeated two more times, and then the termination of the reaction was confirmed by $^{19}F$ NMR. An organic layer was separated from a reaction solution consisting of two layers and condensation and drying were conducted thereon, thereby obtaining 290 g of sodium 1,1-difluoro-2-(pivaloyloxy)ethanesulfinic acid in the form of a white solid (60% yield, 65% purity).

In the reaction solution separated into two layers, the water layer had a fluorine ion concentration of 200 ppm. The organic layer was condensed in a glass flask, by which the glass flask was devitrified.

Thus, sodium hydrogencarbonate used as a base brings about the necessity of the frequent addition of sodium dithionite in order to finish the reaction. Furthermore, glass appliances are to be corroded under the influence of free fluorine ions.

COMPARATIVE EXAMPLE 2-1

Production of Sodium 1,1-difluoro-2-(pivaloyloxy)ethanesulfonic acid (The 2nd Process: Oxidation Process)

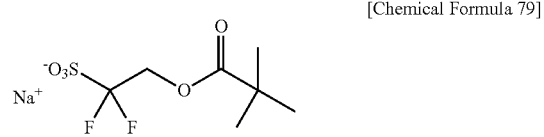

[Chemical Formula 79]

A glass flask equipped with a thermometer, a condenser and a dropping funnel was charged with 290 g (0.74 mole) of 65% purity sodium 1,1-difluoro-2-(pivaloyloxy)ethane-1-sulfinic acid obtained by Comparative Example 1-2, a catalytic amount of sodium tungstate(IV) dehydrate and 600 ml of water, followed by stirring. Then, 170 g (1.5 moles) of 30% hydrogen peroxide solution was added dropwise in an iced bath. After the termination of the dropping, stirring was conducted for 1 hour at room temperature. Then, the termination of the reaction was confirmed by $^{19}F$ NMR. The reaction solution was condensed and then rinsed with 500 ml of diisopropyl ether. Subsequently, filtration was conducted and a solid obtained therewith was dried, thereby obtaining 278 g of sodium 1,1-difluoro-2-(pivaloyloxy)ethanesulfonic acid in the form of a white solid (91% yield, 65% purity). In this case, 2-bromo-2,2-difluoroethyl pivalate was detected to be formed as a by-product in an amount of 8%.

COMPARATIVE EXAMPLE 2-2

Production of Sodium 2-(1'-adamantane)carbonyloxy-1,1-difluoroethane sulfonic acid (The 2nd Process: Oxidation Process)

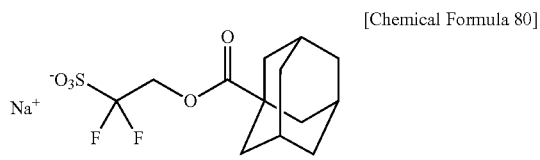

[Chemical Formula 80]

A 300 mL reactor was charged with 18.6 g (64% purity, 36.0 millimoles) of sodium 2-(1'-adamantane)carbonyloxy-1,1-difluoroethanesulfinic acid, 120 mL of water, 0.0154 g (0.047 millimole/0.0013 equivalent) of disodium tungstate dihydrate and 6.1 g (53.9 millimoles/1.5 equivalents) of 30% hydrogen peroxide solution, followed by stirring at room temperature for 2 hours. A reaction solution was heated under a reduced pressure to evaporate a volatile component to dryness, thereby obtaining 18.6 g of the target sodium 2-(1'-adamantane)carbonyloxy-1,1-difluoroethanesulfonic acid. In this case, the purity was 65% and the yield was 97%.

COMPARATIVE EXAMPLE 2-3

Production of Triethylammonium 2-(1-adamantane)carbonyloxy-1,1-difluoroethanesulfonate (The 2nd Process: Oxidation Process)

[Chemical Formula 8]

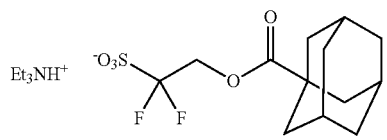

A 200 mL vessel was charged with 18.0 g (97% purity, 54.0 millimoles) of 2'-bromo-2',2'-difluoroethyl 1-adamantanecarboxylate, 50 g of acetonitrile, 40 g of water, 15.0 g (86.4 millimoles/1.6 equivalents) of sodium dithionite and 9.8 g of triethylamine in this order, followed by stirring at room temperature for 1 hour. A reaction solution was separated (without rinsing with water and without rinsing with a sodium thiosulfate aqueous solution or a sodium sulfite aqueous solution) and thereafter a solvent was distilled out of an organic layer, thereby obtaining 27.5 g of the target triethylammonium 2-(1-adamantane)carbonyloxy-1,1-difluoroethanesulfinate. In this case, the purity was 65% and the yield was 81%.

27.5 g of the obtained triethylammonium 2-(1-adamantane)carbonyloxy-1,1-difluoroethanesulfinate (65% purity, 43.7 millimoles), 100 mL of water, 0.021 g (0.066 millimole/0.0015 equivalent) of disodium tungstate dehydrate and 7.0 g (61.2 millimoles/1.4 equivalents) of 30% hydrogen peroxide solution were added, followed by stirring for 3 hours at room temperature. Thereafter, this reaction solution was checked by using $^{19}$F NMR, with which it was confirmed that triethylammonium 2-(1-adamantane)carbonyloxy-1,1-difluoroethanesulfinate was completely consumed and that (2'-bromo-2',2'-difluoro) ethyl 1-adamantanecarboxylate formed as a by-product was 18%. The reaction solution was extracted with 40 mL of dichloromethane two times, and then dichloromethane was distilled out of the obtained organic layer, followed by drying the obtained solid. The solid was dissolved in methanol and then an insoluble residue was separated off by filtration, thereby obtaining a methanol solution. The obtained methanol solution was added dropwise to isopropyl ether, followed by stirring for 1 hour at room temperature. Upon this, a precipitated solid was separated by filtration and dried, thereby obtaining 11.9 g of the target triethylammonium 2-(1-adamantane)carbonyloxy-1,1-difluoroethanesulfonate. In this case, the purity was 97% and the yield was 64%.

If a solvent was distilled out of the organic layer without rinsing with water or without ringing with the sodium thiosulfate aqueous solution or the sodium sulfite aqueous solution in the sulfination process, (2'-bromo-2',2'-difluoro)ethyl 1-adamantanecarboxylate is formed as a by-product in the next process (i.e., the oxidation process).

COMPARATIVE EXAMPLE 3

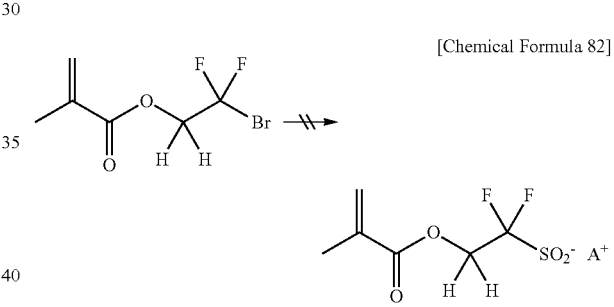

[Chemical Formula 82]

A glass flask equipped with a thermometer and a condenser was charged with 5 g (21.8 millimoles) of 2-bromo-2,2-difluoroethyl (2-methylacrylate), 40 g of acetonitrile and 40 g of water, followed by stirring. The flask was further charged with 3.0 g (30 millimoles) of triethylamine and 5.7 g (32.7 millimoles) of sodium dithionite, followed by stirring for 2 hours at 60° C. An organic layer of a reaction solution was analyzed by using nuclear magnetic resonance (NMR), by which there was not detected the target sodium 1,1-difluoro-2-(2-methacryloyloxy)-ethanesulfinic acid but detected generally only a by-product formed from decomposed methacryl moiety.

COMPARATIVE EXAMPLE 4

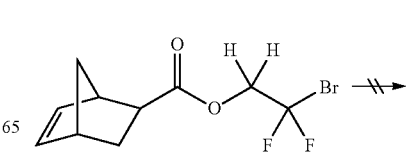

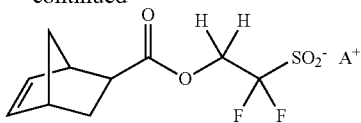

A glass flask equipped with a thermometer and a condenser was charged with 6.13 g (21.8 millimoles) of 5-norbornene-2-carboxylic acid 2-bromo-2,2-difluoroethyl ester, 40 g of acetonitrile and 40 g of water, followed by stirring. The flask was further charged with 3.0 g (30 millimoles) of triethylamine and 5.7 g (32.7 millimoles) of sodium dithionite, followed by stirring for 2 hour at 60° C. An organic layer of a reaction solution was analyzed by using nuclear magnetic resonance (NMR), by which there was not detected the target sulfinic acid salt but detected generally only a by-product having such a moiety as to lose a double bond.

As is evident from Comparative Examples 3 and 4, it is difficult to promote a corresponding sulfination if using a substrate having at R an unconjugated unsaturated moiety (a C=C bond) as a raw material for the 1st process (the sulfination reaction).

COMPARATIVE EXAMPLE 5-1

Production of Triphenylsulfonium 2-hydroxy-1,1-difluoroethanesulfonate (The 4'th Process: Onium-Salt Exchanging Process 2)

[Chemical Formula 84]

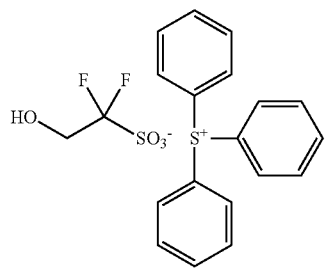

A 2 L reactor was charged with 183.7 g (38% purity, 0.38 mole) of sodium 2-hydroxy-1,1-difluoroethanesulfonic acid, 300 mL of water, 450 mL of chloroform and an aqueous solution of triphenylsulfonium chloride [142.8 g (0.49 mole/1.25 equivalents) of triphenylsulfonium chloride and 150 mL of water], followed by stirring at room temperature for 1 hour. A reaction solution was analyzed by using nuclear magnetic resonance (NMR), by which there was found almost half the raw material sodium 2-hydroxy-1,1-difluoroethanesulfonic acid remaining. Accordingly, the reactor was further charged with the aqueous solution of triphenylsulfonium chloride [142.8 g (0.49 mole/1.25 equivalents) of triphenylsulfonium chloride and 150 mL of water], followed by stirring at room temperature for 0.5 hour (triphenylsulfonium chloride was used in an amount of 285.7 g (0.96 mole/2.5 equivalents) in total and the reaction time was 1.5 hours in total). The reaction solution was analyzed by using nuclear magnetic resonance (NMR), by which the raw material was detected being consumed. Thereafter, the reaction solution was separated. The obtained water layer was extracted with 100 mL of chloroform three times while distilling a solvent out of the obtained organic layer, thereby obtaining 328.2 g of the target triphenylsulfonium 2-hydroxy-1,1-difluoroethanesulfonate. In this case, the purity was 48% and the yield was 97%.

In order to achieve the onium-salt exchange, it is thus necessary to use a monovalent onium salt represented by $Q^+X^-$ (the formula [7]) in an amount not less than 2 equivalents.

COMPARATIVE EXAMPLE 5-2

Production of Triphenylsulfonium 1,1-difluoro-2-(2-methacryloyloxy)-ethanesulfonate (The 5'th Process: Esterification Process 2)

[Chemical Formula 85]

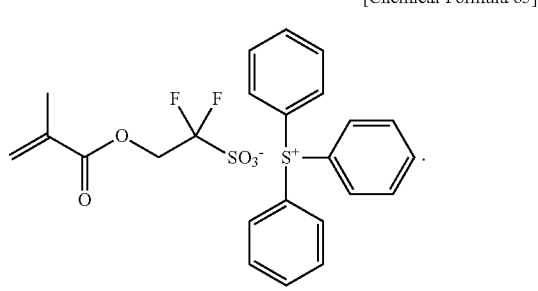

A 2 L reactor was charged with 300.7 g (48% purity, 0.34 mole) of triphenylsulfonium 2-hydroxy-1,1-difluoroethanesulfonate, 700 mL of acetonitrile, 104.8 g (0.68 mole/2 equivalents) of methacrylic anhydride, 8.3 g (0.07 mole/0.2 equivalent) of 4-dimethylaminopyridine, 34.4 g (0.34 mole/1 equivalent) of triethylamine and 60 mg (0.18 millimole) of nonflex MBP, followed by stirring at 50° C. for 2 hours. Then, a solvent was distilled off and 500 mL of chloroform was added thereto, thereby obtaining a chloroform solution. Thereafter, the solution was rinsed with diluted hydrochloric acid and water, and then a solvent was distilled off. The obtained organic substance was rinsed with 300 mL of diisopropyl ether three times, followed by adding 60 mg (0.18 millimole) of nonflex MBP and 300 mL of methyl ethyl ketone. A residual diisopropyl ether was distilled off, thereby obtaining 129.5 g of the target triphenylsulfonium 1,1-difluoro-2-(2-methacryloyloxy)-ethanesulfonate in the form of a viscous liquid. This liquid had difficulty in crystallizing, so that a further purification could not be achieved. Accordingly, the liquid was diluted with methyl ethyl ketone thereby obtaining 440.5 g of 29.4 wt % methyl ethyl ketone solution. In this case, the purity was 98% and the yield was 77%.

In this process, the target substance cannot be crystallized, so that it is difficult to further improve the purity thereof.

TEST EXAMPLE 1

Photoacid Generation Function of Triphenylsulfonium 2-(1-adamantane)carbonyloxy-1,1-difluoroethanesulfonate An acetonitrile solution of sodium 2-(1'-adamantane)carbonyloxy-1,1-difluoroethanesulfonic acid synthesized in Example 8 was prepared to have a concentration of 0.05 mol/L. It was put into a quartz optical cell having an optical path length of 1 cm, followed by irradiation with a light (290 nm) separated from a xenon lamp to conduct actinometry of acid generation. The amount of acid generated was observed by absorption of tetrabromophenol blue at 610 nm. Quantity of light was measured with potassium iron trioxalate to determine quantum yield. With this, it was 0.21 showing a high acid generation function.

TEST EXAMPLE 2

Solubility of Triphenylsulfonium 2-(1-adamantane)carbonyloxy-1,1-difluoroethanesulfonate 1.0 g of sodium 2-(1'-adamantane)carbonyloxy-1,1-difluoroethanesulfonic acid synthesized in Example 8 was weighed and added to 100 g of propylene glycol methyl ether acetate, followed by stirring. With this, it was completely dissolved.

APPLICATION EXAMPLE 1

A resist was prepared by dissolving 2 parts by weight of triphenylsulfonium 1,1-difluoro-2-(valeryloxy)ethanesulfonate mentioned in Example 7, 100 parts by weight of a polymer having a weight average molecular weight of 15,000, in which hydroxyl groups of polyhydroxystyrene have been protected with 15 mol % of 1-ethoxyethyl group and 15 mol % of tert-butoxycarbonyl group, and 0.2 part by weight of isopropanolamine in 600 parts by weight of propylene glycol monomethyl ether acetate.

APPLICATION EXAMPLE 2

A resist was prepared by dissolving 2 parts by weight of triphenylsulfonium 2-(1-adamantane)carbonyloxy-1,1-difluoroethanesulfonate mentioned in Example 8, 100 parts by weight of a polymer having a weight average molecular weight of 15,000, in which hydroxyl groups of polyhydroxystyrene have been protected with 35 mol % of 1-ethoxyethyl group, and 0.2 parts by weight of isopropanolamine in 600 parts by weight of propylene glycol monomethyl ether acetate.

APPLICATION EXAMPLE 3

A resist was prepared by dissolving 5 parts by weight of triphenylsulfonium 2-(1-adamantane)carbonyloxy-1,1-difluoroethanesulfonate mentioned in Example 8, 100 parts by weight of a terpolymer (weight average molecular weight 12800) of 45 mol % methyladamantanemethacrylate/25 mol % hydroxyadamantanemethacrylate/30 mol γ-butyrolactonemethacrylate, and 0.1 part by weight of triethanolamine in 800 parts by weight of propylene glycol monomethyl ether acetate.

TEST EXAMPLE 3

The resists of Application Examples 1, 2 and 3 were filtered by a membrane filter of 0.2 μm to prepare radiosensitive resin composition solutions. Then, the composition solutions were applied on silicon wafers with a rotation speed of 1500 rpm. Then, they were dried at 100° C. for 90 seconds on a hot plate to form resist films having a film thickness of 320 nm. The obtained films were homogeneous and good.

This resist film was subjected to exposure by using an ultraviolet ray by a high-pressure mercury light. After exposure, heating was conducted on the hot plate at 110° C. for 90 seconds. An immersion phenomenon was conducted for 60 seconds in 2.38% tetramethylammonium hydroxide aqueous solution, followed by rinsing with pure water for 30 seconds.

As a result, in all of Application Examples 1, 2 and 3 there were obtained rectangular, positive-type, good patterns having less edge roughness.

Regarding sulfonium salts (PAG 1 and 2) represented by the following formulas, there were conducted evaluations of compatibility and resolution when used for resists.

[Chemical Formula 86]

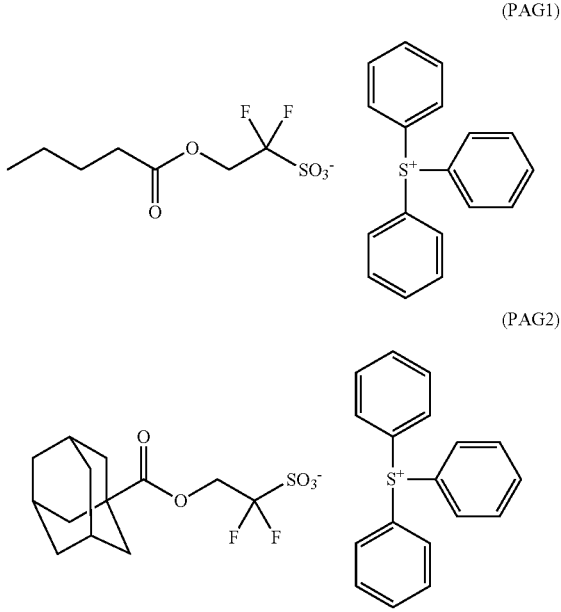

TEST EXAMPLES 4 to 11

Evaluations of PAG Compatibility and Resist Resolution

A resist material was prepared by using a sulfonium salt (PAG 1 or 2) represented by the above formula as an acid generator and a polymer (resin 1-4) represented by the following formula as a base resin. Furthermore, each composition was filtered by a membrane filter of 0.2 μm to prepare each resist solution.

Then, all of the resist solutions were applied to silicon wafers by spin coating to obtain resist films having a film thickness of 250 nm. After conducting a prebaking at 110° C., exposure was conducted with 248 nm ultraviolet ray through a photomask, and then a post-exposure baking was conducted at 120° C. After that, development was conducted at 23° C. for 1 minute by using 2.38 wt % tetramethylammonium hydroxide aqueous solution. Composition and evaluation results of each resist are shown in Table 1.

TABLE 1

| Test Example | Resin (parts by wt.) | Acid Generator (parts by wt.) | Solvent (parts by wt.) | Compatibility | Pattern Shape |
|---|---|---|---|---|---|
| 4 | Resin 1 (40) | PAG1 (1.0) | PGMEA (400) | Good | Clean rectangular |
| 5 | Resin 1 (40) | PAG2 (1.0) | PGMEA (400) | Good | Clean rectangular |
| 6 | Resin 2 (40) | PAG1 (1.0) | PGMEA (400) | Good | Clean rectangular |

TABLE 1-continued

| Test Example | Resin (parts by wt.) | Acid Generator (parts by wt.) | Solvent (parts by wt.) | Compatibility | Pattern Shape |
|---|---|---|---|---|---|
| 7 | Resin 2 (40) | PAG2 (1.0) | PGMEA (400) | Good | Clean rectangular |
| 8 | Resin 3 (40) | PAG1 (1.0) | PGMEA (400) | Good | Clean rectangular |
| 9 | Resin 3 (40) | PAG2 (1.0) | PGMEA (400) | Good | Clean rectangular |
| 10 | Resin 4 (40) | PAG1 (1.0) | PGMEA (400) | Good | Clean rectangular |
| 11 | Resin 4 (40) | PAG2 (1.0) | PGMEA (400) | Good | Clean rectangular |

COMPARATIVE EXAMPLES 6 to 13

With respect to sulfonium salts (PAG 3 and 4) represented by the following formulas, evaluations of compatibility of PAG used for resists and resolution of the resists are shown in Table 2 for comparison.

[Chemical Formula 87]

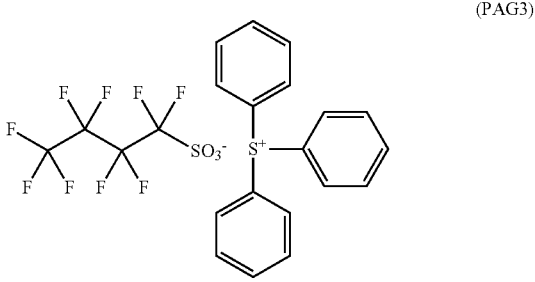

(PAG3)

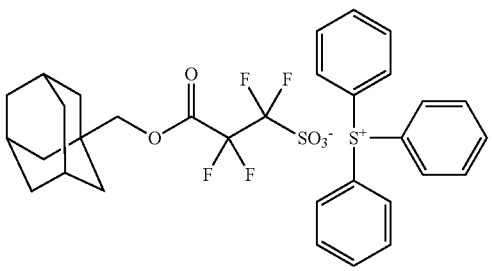

(PAG4)

TABLE 2

| Comparative Example | Resin (parts by wt.) | Acid Generator (parts by wt.) | Solvent (parts by wt.) | Compatibility | Pattern Shape |
|---|---|---|---|---|---|
| 6 | Resin 1 (40) | PAG3 (1.0) | PGMEA (400) | Good | Somewhat head-swollen shape |
| 7 | Resin 1 (40) | PAG4 (1.0) | PGMEA (400) | Good | Somewhat distorted rectangular |
| 8 | Resin 2 (40) | PAG3 (1.0) | PGMEA (400) | Somewhat defective | Somewhat head-swollen shape |
| 9 | Resin 2 (40) | PAG4 (1.0) | PGMEA (400) | Good | Clean rectangular (inferior to Test Example 7) |
| 10 | Resin 3 (40) | PAG3 (1.0) | PGMEA (400) | Somewhat defective | Somewhat head-swollen shape |
| 11 | Resin 3 (40) | PAG4 (1.0) | PGMEA (400) | Good | Clean rectangular (inferior to Test Example 9) |
| 12 | Resin 4 (40) | PAG3 (1.0) | PGMEA (400) | Somewhat defective | Somewhat head-swollen shape |
| 13 | Resin 4 (40) | PAG4 (1.0) | PGMEA (400) | Good | Somewhat distorted rectangular (inferior to Test Example 11) |

From the results shown in Table 1 and Table 2, it was confirmed that the acid generator of the present invention had a resolution higher than those of conventional products.

The invention claimed is:

1. A method for producing a 2-(alkylcarbonyloxy)-1,1-difluoroethanesulfonic acid onium salt represented by a formula [5]

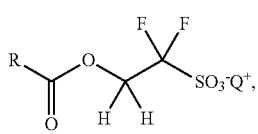

[5]

comprising the step of:
carrying out an onium-salt exchange on the 2-(alkylcarbonyloxy)-1,1-difluoroethanesulfonic acid ammonium salt represented by a formula [3], by using a monovalent onium salt represented by a formula [4]

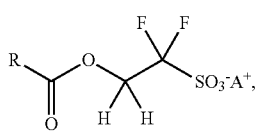

[3]

wherein the 2-(alkylcarbonyloxy)-1,1-difluroethanesulfonic acid ammonium salt represented by a formula [3] is obtained by
a 1st process (a sulfination process) reacting a carboxylic acid bromodifluoroethyl ester represented by a formula [1]

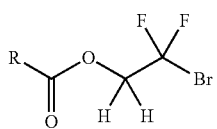

[1]

with a sulfinating agent in the presence of an amine thereby obtaining a 2-(alkylcarbonyloxy)-1,1-difluoroethanesulfinic acid ammonium salt represented by a formula [2]

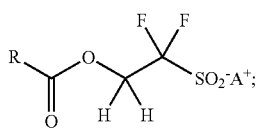

[2]

and
a 2nd process (an oxidation process) reacting the 2-(alkylcarbonyloxy)-1,1-difluoroethanesulfinic acid ammonium salt represented by the formula [2] and obtained by the 1st process (the sulfination process) with an oxidizing agent thereby obtaining a 2-(alkylcarbonyloxy)-1,1-difluoroethanesulfonic acid ammonium salt represented by the formula [3],
wherein R represents a linear or branched alkyl group having 1 to 10 carbon atoms, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms, wherein some or all of hydrogen atoms in each of the alkyl group, the alicyclic organic group, the organic group containing the alicyclic organic group and the linear alkylene group, the monocyclic or polycyclic lactone and the aryl group may be substituted with fluorine, a hydroxyl group, a hydroxycarbonyl group, or a linear, branched or cyclic alkoxy group having 1 to 6 carbon atoms, wherein two hydrogen atoms on the same carbon that constructs the alkyl group, the alicyclic organic group, or the organic group containing the alicyclic organic group and the linear alkylene group may be substituted with one oxygen atom to form a keto group, wherein those who have in its R structure an unconjugated unsaturated moiety (a double or triple bond) are excepted, and wherein $A^+$ represents an ammonium ion, wherein $X^-$ represents a monovalent anion, wherein $Q^+$ is a sulfonium cation represented by a formula (a) or a formula (b), or an iodonium cation represented by a formula (c)

(a)

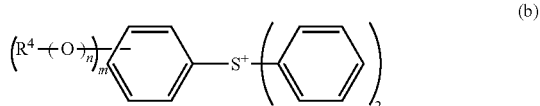

(b)

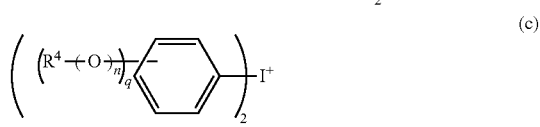

(c)

wherein $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms, wherein any two or more of $R^1$, $R^2$ and $R^3$ may bond to each other to form a ring together with a sulfur atom shown in the formula, wherein $R^4$ represents a substituted or unsubstituted linear, branched or cyclic alkyl group or alkenyl group having 1 to 20 carbon atoms or a substituted or unsubstituted aryl group having 6 to 14 carbon atoms, wherein m represents an integer of between 1 and 5, wherein n represents 0 or 1, and wherein q represents an integer of between 0 and 5.

2. A method as claimed in claim 1, further comprising:
carrying out a reaction of the 2nd process in the presence of disodium tungstate as a transition metal catalyst.

3. A method as claimed in claim 1, wherein the ammonium ion is represented by a formula [I]

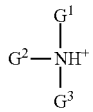

[I]

wherein $G^1$, $G^2$ and $G^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable hetero aromatic group having 5 to 10 carbon atoms, and wherein at least two or more of $G^1$, $G^2$ and $G^3$ may represent a ring which may include a hetero atom.

4. A method as claimed in claim 2, wherein the ammonium ion is represented by a formula [I]

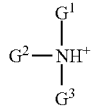

[I]

wherein $G^1$, $G^2$ and $G^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms, and wherein at least two or more of $G^1$, $G^2$ and $G^3$ may represent a ring which may include a hetero atom.

* * * * *